(12) United States Patent
Forster et al.

(10) Patent No.: US 11,406,976 B2
(45) Date of Patent: Aug. 9, 2022

(54) MICROFLUIDIC DEVICE FOR DETECTION OF ANALYTES

(71) Applicant: Dublin City University, Dublin (IE)

(72) Inventors: Robert Forster, Dublin (IE); Elaine Spain, Dublin (IE); Kellie Adamson, Swords (IE); Eadaoin Carthy, Paulstown (IE); David Boyle, Dublin (IE)

(73) Assignee: DUBLIN CITY UNIVERSITY, Dublin (IE)

( * ) Notice: Subject to any disclaimer, the term of this patent is extended or adjusted under 35 U.S.C. 154(b) by 387 days.

(21) Appl. No.: 16/500,190

(22) PCT Filed: Mar. 28, 2018

(86) PCT No.: PCT/EP2018/057997
§ 371 (c)(1),
(2) Date: Oct. 2, 2019

(87) PCT Pub. No.: WO2018/184957
PCT Pub. Date: Oct. 11, 2018

(65) Prior Publication Data
US 2021/0106991 A1   Apr. 15, 2021

(30) Foreign Application Priority Data

Apr. 3, 2017  (GB) .................................... 1705328

(51) Int. Cl.
*B01L 3/00* (2006.01)
*G01N 27/07* (2006.01)
(Continued)

(52) U.S. Cl.
CPC ........ *B01L 3/502715* (2013.01); *G01N 27/07* (2013.01); *G01N 33/5438* (2013.01);
(Continued)

(58) Field of Classification Search
CPC ......... B01L 2200/00; B01L 2200/0621; B01L 2200/0668; B01L 2200/0684;
(Continued)

(56) References Cited

U.S. PATENT DOCUMENTS 5,922,604 A * 7/1999 Stapleton ............... B01L 3/5027
  436/46
6,315,940 B1   11/2001 Nisch et al.
(Continued)

FOREIGN PATENT DOCUMENTS

EP   1628768 A2   3/2006
WO   0036145 A1   6/2000
(Continued)

OTHER PUBLICATIONS

International Preliminary Report on Patentability with Written Opinion dated Oct. 17, 2019 for International Application No. PCT/EP2018/057997, 9 pages.
(Continued)

*Primary Examiner* — Jennifer Wecker
*Assistant Examiner* — Jonathan Bortoli
(74) *Attorney, Agent, or Firm* — Cozen O'Connor

(57) ABSTRACT

A microfluidic device for detection of an analyte in a fluid is described. The microfluidic device comprises a substrate having a first surface defining entrances to one or more chambers defined in the substrate, surfaces of the chambers defining a second surface of the substrate, the first surface being modified for selective targeting and capture of at least one analyte to operably effect a blocking of the entrance to at least one of the chambers, and wherein a response characteristic of the microfluidic device is operably varied by the blocking of the entrance to the at least one of the chambers, thereby providing an indication of the presence of the analyte within the fluid.

32 Claims, 23 Drawing Sheets

(51) Int. Cl.
*G01N 33/543* (2006.01)
*G01N 33/569* (2006.01)
*G01N 33/577* (2006.01)
*G01N 35/00* (2006.01)

(52) U.S. Cl.
CPC . *G01N 33/56911* (2013.01); *G01N 33/56961* (2013.01); *G01N 33/577* (2013.01); *G01N 35/00069* (2013.01); *B01L 2200/0621* (2013.01); *B01L 2200/10* (2013.01); *B01L 2300/0645* (2013.01); *B01L 2300/0803* (2013.01); *B01L 2300/087* (2013.01); *G01N 2333/195* (2013.01); *G01N 2333/37* (2013.01)

(58) Field of Classification Search
CPC ......... B01L 2200/10; B01L 2300/0645; B01L 2300/0803; B01L 2300/087; B01L 2300/161; B01L 2400/04; B01L 2400/0406; B01L 2400/0409; B01L 2400/043; B01L 2400/0677; B01L 2400/088; B01L 3/502715; B01L 3/502723; B01L 3/50273; B01L 3/502738; B01L 3/502746; B01L 3/502761; G01N 2333/195; G01N 2333/37; G01N 27/07; G01N 33/54366; G01N 33/5438; G01N 33/56911; G01N 33/56961; G01N 33/577; G01N 35/00069
See application file for complete search history.

(56) References Cited

U.S. PATENT DOCUMENTS

| | | | |
|---|---|---|---|
| 2006/0068409 A1 | 3/2006 | Phan et al. | |
| 2008/0130003 A1 | 6/2008 | Kuroda et al. | |
| 2008/0300148 A1 | 12/2008 | Lee et al. | |
| 2011/0192726 A1* | 8/2011 | Chen | A61B 5/14546 204/547 |
| 2011/0195852 A1* | 8/2011 | Walt | G01N 33/54366 506/9 |
| 2015/0004627 A1* | 1/2015 | Wu | G01N 33/5438 435/7.8 |
| 2017/0010259 A1* | 1/2017 | Amoabediny | G01N 33/5438 |

FOREIGN PATENT DOCUMENTS

| | | | | |
|---|---|---|---|---|
| WO | 2014206968 A1 | 12/2014 | | |
| WO | WO-2015187792 A1 * | 12/2015 | ......... | G01N 33/6854 |
| WO | 2017027384 A1 | 2/2017 | | |

OTHER PUBLICATIONS

Combined Search and Examination Report under Sections 17 and 18(3) for Application No. GB1705328.1 dated Oct. 2, 2017 in 6 pages.
International Search Report and Written Opinion for International Application No. PCT/EP2018/057997 dated May 14, 2018 in 15 pages.

* cited by examiner

Introducing a fluid to a microfluidic device
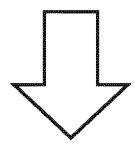
Inducing a fluid flow
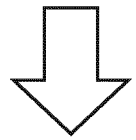
Capturing an analyte
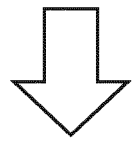
Detecting presence of the analyte in a fluid by measuring a variation in a response characteristic of the microfluidic device
Figure 5B

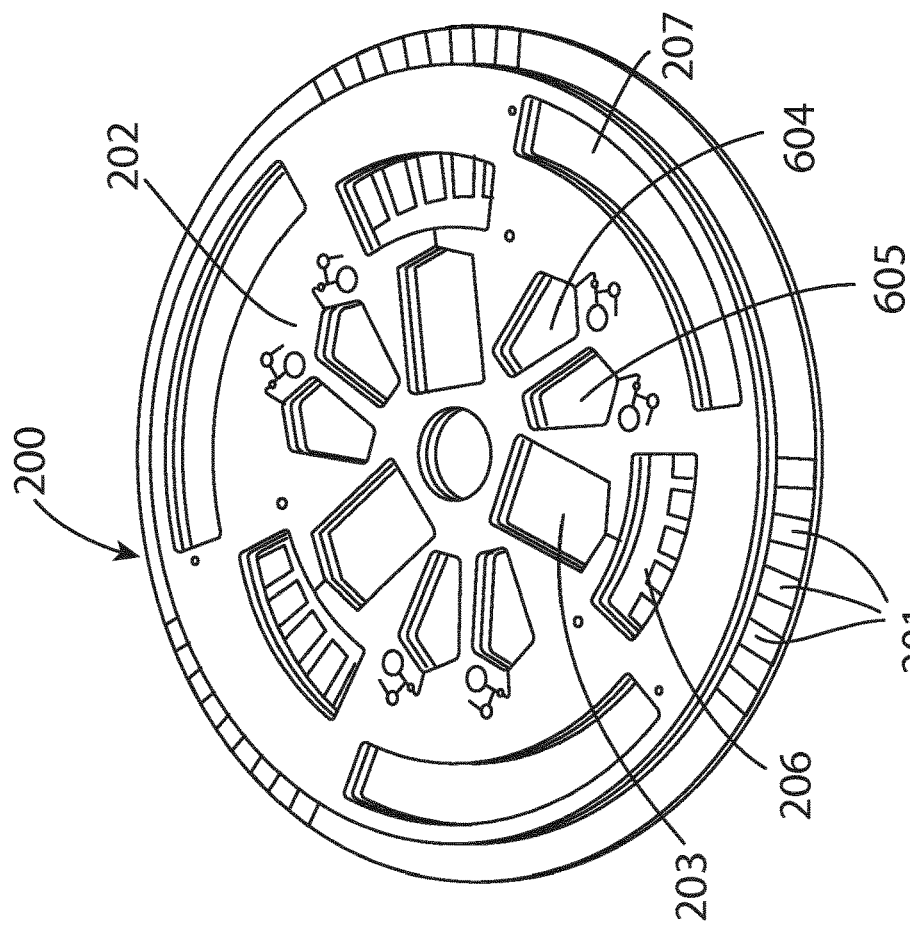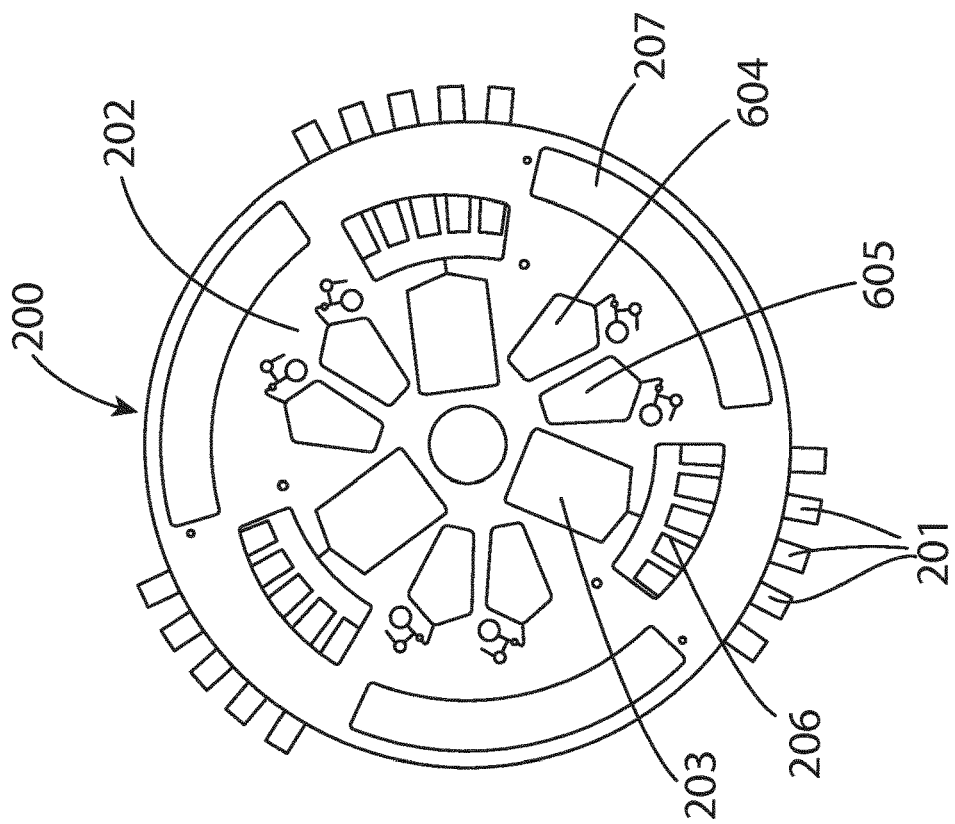
Figure 7B

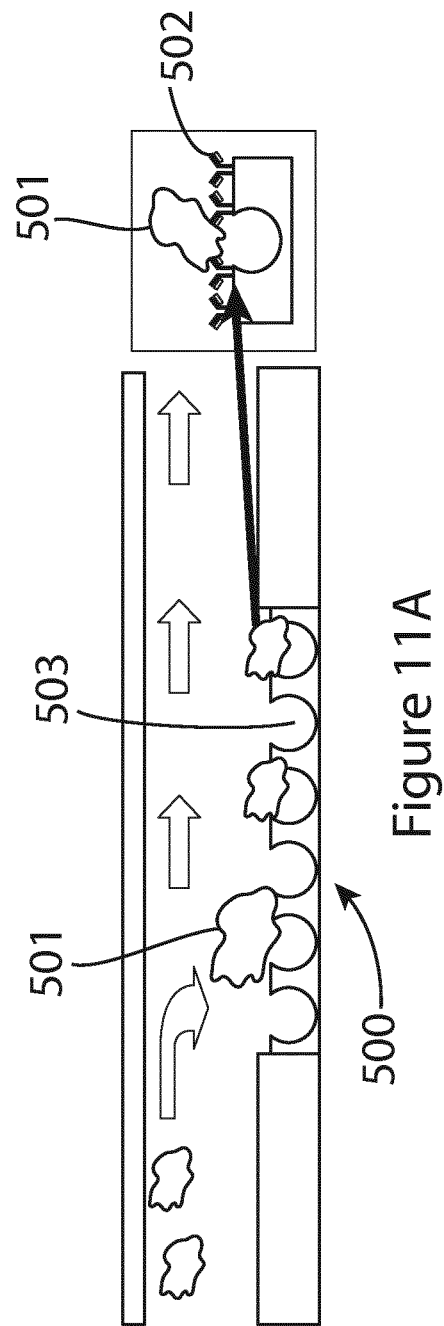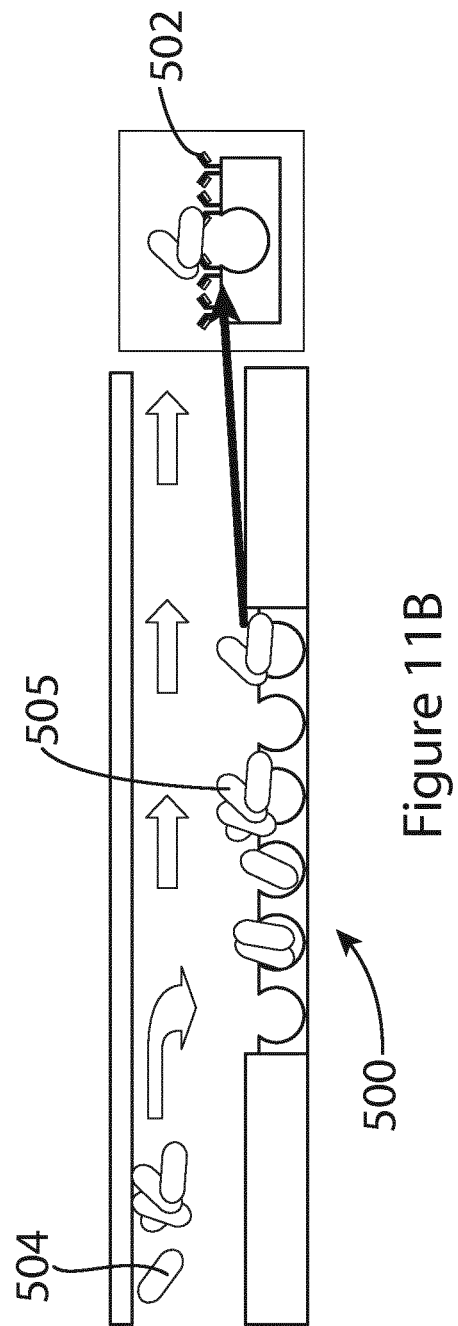

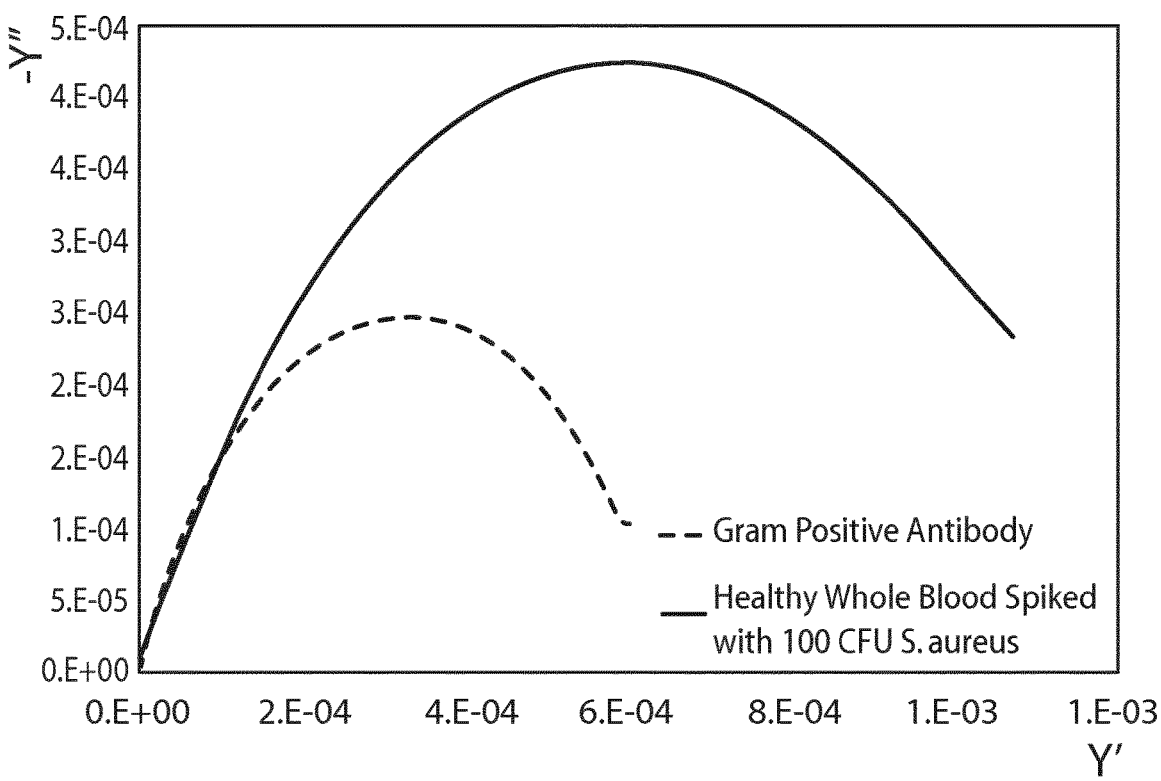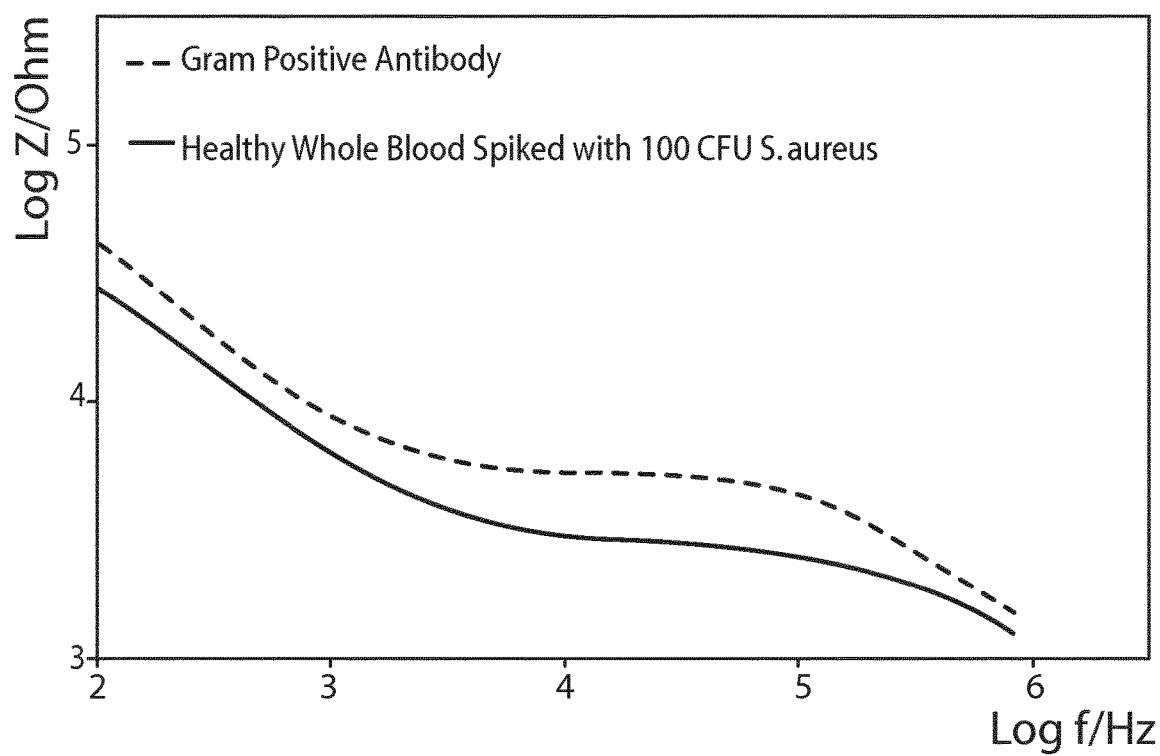
Figure 14

2 Micron Diameter Cavities     1 Micron Diameter Cavities
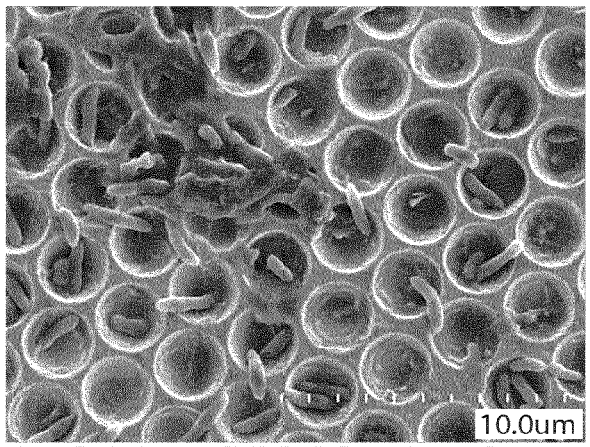
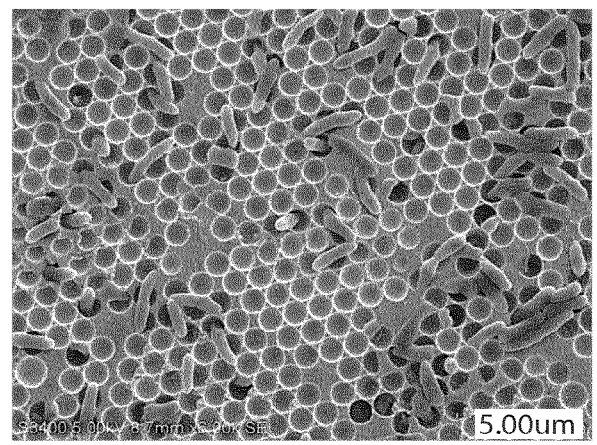
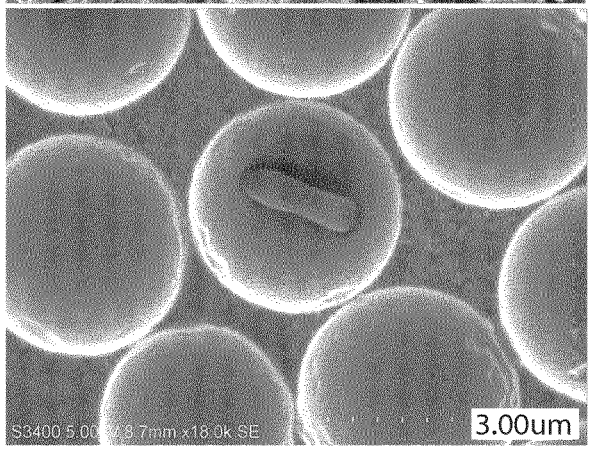
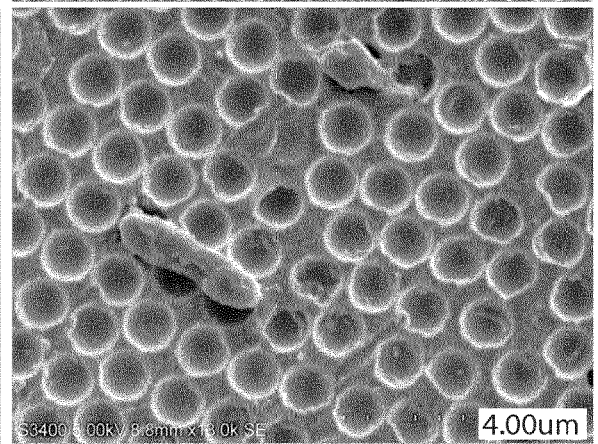
Figure 15

MICROFLUIDIC DEVICE FOR DETECTION OF ANALYTES

FIELD

The present application relates to microfluidic devices and in particular to microfluidic devices that are configured for detection of an analyte, where said analyte is a microscopic object, for example, a specific type of cell, within a fluid. The application particularly relates to a microfluidic device that is configured for capture and detection of an analyte within a fluid sample whereby capture of an analyte is indicated by a change in a response characteristic of the microfluidic device. The device directly detects the target analyte at low concentration without amplification, for example, by blood culture (cellular analyte). Once the microscopic object is captured, a molecular analyte can be detected at low concentration without amplification, for example, by polymerase chain reaction, PCR (nucleic acid analyte).

BACKGROUND

The detection of rare cells has important implications for the diagnosis, theranosis and prognosis of diseases including blood borne infection, sepsis, and the metastasis of cancer through circulating tumour cells.

For example, many deaths caused by pathogens could be prevented through, highly sensitive, rapid, point of care diagnostic tools. Microfluidic devices capable of detecting the presence of pathogens in clinical samples and providing additional information about the identity and properties of the pathogens are highly desirable.

Early detection of cell based diseases from sepsis to metastatic cancer allows the most appropriate therapeutic measures to be started rapidly, e.g., antibiotic or antineoplastic medication, but current detection strategies are too insensitive requiring the concentration of the target analyte to be increased or be amplified, for example, by blood culture.

A second key issue is the sample-to-answer time and current technologies often take extended periods to produce a result. For example, culturing blood borne pathogens can take up to three days followed by PCR for pathogen identification. There are also certain limitations to blood cultures. For example, blood cultures are positive in only 30-40% of patients with severe sepsis and septic shock. Moreover, early in the infection the bacterial loads are low, i.e. 1-10 CFU/ml requiring long culture times. Studies have shown clinically significant bacteraemia in adults is characterized by low pathogen numbers, for example, 10 CFU/ml in 73% of adults with gram-negative bacteraemia and 1-30 CFU/ml in more than half of adult patients with staphylococcal and streptococcal endocarditis. Fastidious, or viable but non-culturable, VBNC, pathogens may not grow at all leading to false negatives. In addition, blood cultures will be sub-optimal in the case of samples from patients treated with antibiotics before the blood draw.

Several new technologies have been introduced that speed up diagnosis, such as: automated continuous culture systems, rapid pathogen identification using matrix-assisted laser desorption ionization time-of-flight (MALDITOF) (e.g. Bruker MALDI Biotyper™+Sepsityper®), and automated systems for antimicrobial susceptibility testing. However, these methods are high cost, labour intensive and most importantly, are performed in a centralised laboratory. Moreover, the detection sensitivity of many commercially available methods is intrinsically poor (hence the need for amplification of the analyte) which compromises the accuracy and leads to relatively high false negatives especially early on in bacteraemia.

Cellular assays using both blood culture and whole blood samples are commercially available, but are predominantly based in a centralised testing laboratory. They have had a very limited impact on clinical practice and have not been widely adopted. In cases where they have been adopted, they are used to complement rather than replace conventional culture-based approaches.

Examples of commercially available methods for pathogen identification and antibiotic susceptibility using positive blood culture samples include: SeptiFast (Roche Molecular Diagnostics), an in vitro nucleic acid amplification test for the detection and identification of bacterial and fungal DNA (15 in total) directly from whole blood using their specific PCR (LightCycler® 2.0) instrument; Prove-it sepsis (Mobidiag, Finland), an in-vitro diagnostic for detecting sepsis-causing pathogens in blood cultures using multiplex PCR (polymerase chain reaction) and microarray; FilmArray Blood Culture Identification Panel (BioFire/bioMeriux) which uses real-time multiplex PCR; Verigene® gram-negative bacteria blood test (Nanosphere) which uses hybridisation on microarray 60 bacteria+13 fungi; and Verigene® gram positive bacteria blood test (Nanosphere) which uses hybridisation on microarray.

However, there are disadvantages of these methods. For example, results are not available sufficiently quickly to inform early antibiotic treatment decisions. For example, the time from 'sample to result' will also include time for blood culture (+24-72 hrs) and time for sample transport and result reporting if lab-based assay (+~4-8 hrs). The methods typically have limited pathogen coverage. They detect only a limited range of pathogens and so cannot replace culture-based/MALDI methods for pathogen identification. Typically, the optimum antibiotic, or the antibiotic resistance status of the organism, is not determined. Thus, pathogen identification and antibiotic susceptibility information is typically not available to inform the initial selection of appropriate antibiotic therapy, so a 'safety first' strategy of administering empirically determined broad-spectrum antibiotics is recommended followed by rapid de-escalation to appropriate monotherapy. This is often not the optimum course of therapy.

In conclusion, there exists a significant unmet medical need for a rapid diagnostic test to aid physicians within the early "golden hours" of diagnosis and consequent treatment in patients presenting with clinical symptoms suggesting sepsis.

SUMMARY

To address these and other issues, the present teaching describes a device and methodology that allows for the highly efficient capture and ultrasensitive detection of a microscopic, typically cellular, analyte within a fluid sample.

Accordingly, the present teaching provides a device and method in accordance with the claims that follow.

The device according to the present teaching achieves direct, highly sensitive detection, that is, detection of a few analytes per ml of sample, through highly efficient capture of the analyte and by amplifying the signal associated with the capture of small numbers of analytes. The microfluidic device described herein dispenses with the need for concentration of the target analyte to be increased or be amplified, for example, by blood culture.

In one aspect, the present teaching provides a microfluidic device that allows the capture and detection of a target cell from a fluid sample, for example, a blood sample.

In particular, the present teaching provides a microfluidic device for detection of an analyte within a fluid, the microfluidic device comprising a substrate having a first surface defining entrances to one or more chambers defined in the substrate, surfaces of the chambers defining a second surface of the substrate. The first surface is modified for selective targeting and capture of at least one analyte to operably effect a blocking of the entrance to at least one of the chambers, and wherein a response characteristic of the microfluidic device is operably varied by the blocking of the entrance to the at least one of the chambers, thereby providing an indication of the presence of the analyte within the fluid.

The blocking of the entrance to at least one of the chambers is effected by a blocking or plugging of the chamber. The blocking or plugging may be achieved by the captured analyte being located across the entrance to the chamber or by the captured analyte being located in the chamber. The blocking or plugging may also be achieved by the captured analyte being at least partially located within the chamber or by the captured analyte being located fully within the chamber thereby blocking the entrance to the chamber. Depending on the diameter of the chamber (cavity) and the size of the analyte, the captured analyte "plugs" inside the chamber (cavity) or "blocks" across the opening of the chamber.

The first surface may be selectively modified to inhibit non-specific capture of analyte, for example, interfering materials within the sample. Selective modification of the first surface controls the positioning of captured or adhered target cells through the location of the deposited capture agent.

The detection surface of the device according to a preferred aspect of the present teaching comprises a capture surface comprising a plurality of chambers within a substrate in which the substrate surface is functionalised with a capture agent for the analyte and the inner surface of the chambers is functionalised with a capture agent for a molecular marker arising from the captured analyte.

The analyte may comprise a biological cell including, for example, a pathogen, cancer cell, or other rare cell. The analyte may, for example, comprise a single pathogen or a colony of pathogens.

The microfluidic device may comprise a substrate comprising an analyte capture substrate that can be substantially planar, or comprise a single or a plurality of chambers (cavities) defined within the substrate.

The analyte capture substrate defines a first, upper, surface of the substrate and containing the chambers (cavities) is modified for selective capture of at least one analyte to effect a blocking of at least one of the chambers, and wherein a response characteristic of the microfluidic device is operably varied by the blocking of at least one of the chambers, thereby providing an indication of the presence of the analyte within the fluid.

The one or more chambers defined in the substrate may have a diameter or width in the range 100 nm to 10 µm. The chambers may have depths between 0.05 and 0.95 times the diameter of the chamber. Chambers of different sizes may be provided on different regions of the first surface of the substrate. The size and shape of the chambers may be selected to match that of the target analyte.

In a preferred aspect, the chambers (cavities) are laterally spaced such that the spacing between the chambers is optimised for the selective and efficient capture of the target analyte to be detected. The spacing between the chambers may inhibit non-specific binding of interferences.

The pitch or separation between the plurality of chamber entrances may be between 0 and one hundred times the chamber diameter.

In one aspect of the microfluidic device according to the present teaching, surfaces of the chambers defined in the substrate define a curved surface.

The first surface of said substrate may be modified by immobilising a capture agent on said surface.

The first surface may be functionalised with an appropriate target analyte capture agent. For example, the target analyte may be a pathogen and a region of the first surface may be functionalised with antibodies for the capture of gram positive bacteria, gram negative bacteria or fungal pathogens. Alternatively, these antibodies could be selective for particular specific targets, e.g., *Staph. aureus*.

The capture antibodies or capture protein may be immobilised in specific regions on the first surface by a variety of techniques, for example, wet chemical deposition, cold plasma deposition or soft stamping onto said surface. In the case of a substantially planar analyte capture substrate, specific capture regions can be defined by the pattern of the capture agent deposited.

The concentration of the capture agent(s) may be higher around the entrance of the one or more chambers (cavities) on the first surface. This arrangement of capture agents promotes site specific binding of the analyte across the chambers. The surface coverage of the capture agent is optimised.

The present teaching provides for tuning the size of the detecting surface so that the same fraction of its surface is covered by analyte (key determinant of S/N (signal to noise) ratio) is optimised even for ultralow concentrations (<pM) of the analyte in solution.

The capture antibodies may comprise commercial or custom engineered antibodies. Engineered recombinant antibody fragments such as small, non-glycosylated Fab and scFv fragments, usually with terminal polypeptides such as cMyc, His or FLAG have recently been favoured for bacteria capture with high affinity.

The capture protein may comprise a yeast protein. The skilled person will appreciate that the capture protein may comprise yeast protein, IgG, IgA, IgM antibodies or anti-*Candida albicans* antibody. Recent eukaryotic cell cultures, such as those of the yeast *Pichia pastoris*, show efficient production of fully processed scFvs (single chain variable fragments) albeit with high-mannose oligosaccharides.

The capture agent may be an aptamer, i.e., single-stranded DNA or RNA (ssDNA or ssRNA) molecules that can bind to pre-selected targets including proteins and peptides with high affinity and specificity.

The capture agent may be a polymer.

The capture agent may be a peptide.

The capture agent may be synthetic or naturally occurring.

The response characteristic of the microfluidic device according to the present teaching comprises an electrochemical signal or optical signal which is operably varied upon capture of an analyte thereby indicating the presence of the target analyte within the fluid.

In a particularly preferred aspect, the electrochemical signal comprises a changed impedance signal (resistance and capacitance) which provides an indication of a cellular concentration, e.g., pathogen load, within the fluid. The signal is quantitative and accordingly provides an indication of cell concentration within the sample.

In a particularly preferred aspect, the electrochemical signal comprises a change in the current associated with oxidation or reduction of a bound or free molecule which provides an indication of the analyte concentration within the fluid.

In an alternative aspect, the optical signal comprises a change in the fluorescence intensity or lifetime of a bound or free luminophore which provides an indication of the analyte concentration within the fluid.

In a further alternative aspect, the optical signal comprises a change in the Raman scattering intensity of a bound or free luminophore which provides an indication of the analyte concentration within the fluid.

In a further aspect of the microfluidic device according to the present teaching, an internal surface of each chamber on the substrate is modified for detection of at least one molecular marker arising from the captured entity, e.g., DNA for cell identification, protein/nucleic acid/small molecule biomarker of a property of the captured cell, such that a response characteristic of the microfluidic device is operably varied by the binding of the released marker into at least one of the chambers. The internal surface of each chamber may be functionalised with a capture agent. The capture agent may comprise any suitable capture agent, for example DNA capture strands, antibodies or synthetic capture agents. The internal surface of each chamber may be functionalised with a monolayer of deoxyribonucleic acid (DNA) or ribonucleic acid (RNA) "capture" strands that can hybridise/anneal to complementary DNA or RNA (target analyte), allowing them to form a single double-stranded molecule through base pairing. In this aspect, the response characteristic of the microfluidic device comprises an electrochemical or optical signal which is operably varied upon capture of the target analyte followed by marker release thereby indicating the presence of an analyte within the fluid.

In a particularly preferred aspect, the electrochemical signal comprises a changed impedance signal (resistance and capacitance) which provides an insight into the identity or properties of the captured analyte. The changed signal also provides an indication of pathogen load within the fluid.

In a particularly preferred aspect, the electrochemical signal comprises a change in the current associated with reduction or oxidation of a bound or free electroactive molecule which provides insight into the identity or properties of the captured analyte.

The time taken for a released marker from a target analyte to bind to the functionalised interior of the cavity depends on the nature of the marker and the capture agents, e.g., it can be as short as one minute for short nucleic acid (NA) strands increasing to 60 min for longer strands, the time also depends on device geometry in particular the cavity size. Typically, sensitivity is increased by allowing the marker to bind to the functionalised cavity surface for longer periods.

The microfluidic device described herein can detect cells at concentrations of about 2 cells/ml.

The fluid sample may be selected from the group consisting of a liquid sample, a whole blood sample, blood plasma or other fraction, interstitial fluid, cerebrospinal fluid, urine or saliva. Minimum sample volumes required are typically for example, in the case of a blood sample (100 µL-6 mL), urine (100 µL-6 mL) or saliva (<1 mL).

Extracted samples may also be tested, such as for example, wound swab extracted into buffer solution or a liquidised food sample.

Typically, the device according to the present teaching allows for detection of the analyte within a timeframe of less than one hour. Such timeframes are highly desirable in a clinical environment allowing rapid administration of antibiotics or elimination of sepsis as the underlying illness. An advantage of the device according to the present teaching is that it provides a rapid and automated device which can test multiple samples in one run.

In a further aspect, the present teaching provides a method of detecting an analyte in a fluid comprising the use of the microfluidic device as described herein. The method comprises the steps of
  (i) introducing a fluid to the microfluidic device according to the present teaching,
  (ii) inducing a fluid flow,
  (iii) capturing an analyte; and
  (iv) detecting the presence of the analyte in the fluid by measuring a variation in a response characteristic of the microfluidic device.

The analyte is captured on the upper surface of the cavity array. The analyte may comprise a (sub)microscopic analyte, for example, a cell, vesicle or exosome.

In a still further aspect, the method may further comprise the step of measuring the release of a marker from the captured entity.

In accordance with the method of the present teaching, the response characteristic of the microfluidic device comprises an electrochemical or optical response, which is operably varied upon capture of an analyte in the fluid.

In a still further aspect, the present teaching provides a microfluidic disc comprising a microfluidic device as described herein.

One incarnation of the microfluidic device involves mounting the functionalised cavity array within an automated centrifugal lab on a disk, LOAD, platform. The LOAD has the advantage of controlling the rotation speed of the centrifugal device to pump fluid and manipulate the transfer of liquids within the device. Due to the architecture of the microchannels and the fluid flow characteristics, the probability of collision between the probe and the analyte is increased by the much shorter diffusion distance. This allows sample movement over the electrode surface in a highly controlled manner so as to ensure maximum interaction of the analyte and the capture surface. The device geometry therefore improves transport of the analyte to multiple capture surface so as to overcome diffusion-limited processes and improve mass transport rates, resulting in reduced analysis times.

The present teaching provides a microfluidic disc with a microfluidic device comprising a functionalised cavity array for the capture and detection of pathogens in a fluid sample.

In another aspect, the present teaching provides a microfluidic device that enables a pathogen subtype to be identified.

The device according to the present teaching is designed for near patient testing by rapidly providing easily interpreted information that directly influences clinical decision making. In a preferred aspect, the device enables the rapid, near patient detection of sepsis, for example.

The device described herein provides rapid detection allowing analysis to be performed more rapidly, less expensively and more reliably than current systems. An advantage of the device according to the present teaching is that it provides rapid assessment of health threats through a short analysis time since the signal, not the target analyte is amplified.

It will be appreciated that the microfluidic device described herein allows for the accurate assessment of disease stage and prognosis for a patient since a wide dynamic range will be achieved by tuning the number of cavities in the array.

The device described herein can be manufactured at a decreased manufacturing cost compared to known centralised laboratory systems.

These and other features and advantages of an approach in accordance with the present teaching will be better understood with reference to the following exemplary arrangements.

BRIEF DESCRIPTION OF THE DRAWINGS

The present application will now be described with reference to the accompanying drawings in which:

FIG. 5B is a flow chart showing the steps of the method of detecting an analyte in a fluid according to the present teaching;

FIG. 7B shows an overview of the device of FIG. 7A, complemented by a trimetric view for 3D representation of the assembled device;

FIG. 11A is a schematic of pathogen capture at the antibody adsorbed cavity array surface;

FIG. 11B is a schematic of pathogen capture at the antibody adsorbed cavity array surface showing single pathogens and colonies of pathogens where depending on the size of the cavity the pathogens either bind across the cavity or into the microcavity (chamber) or both, within one sample;

FIG. 14 shows impedance spectra (Top) presenting a significant change in impedance following successful capture of *S. aureus* pathogens from a spiked healthy whole blood sample onto a photolithography cavity array substrate surface using a PDMS stamp using a 10-minute incubation time and 2 Minute Read Time within the microfluidic incubation chamber; both the Nyquist plot (top) and the bode plot (bottom) show significant changes following pathogen capture; and FIG. 15 highlights what is presented in FIG. 14 and shows SEM images of successful capture of pathogens onto an antibody modified cavity array substrate where cell capture "plugs" inside the cavity or blocks across the opening of the microcavity.

DETAILED DESCRIPTION

Figure 1:
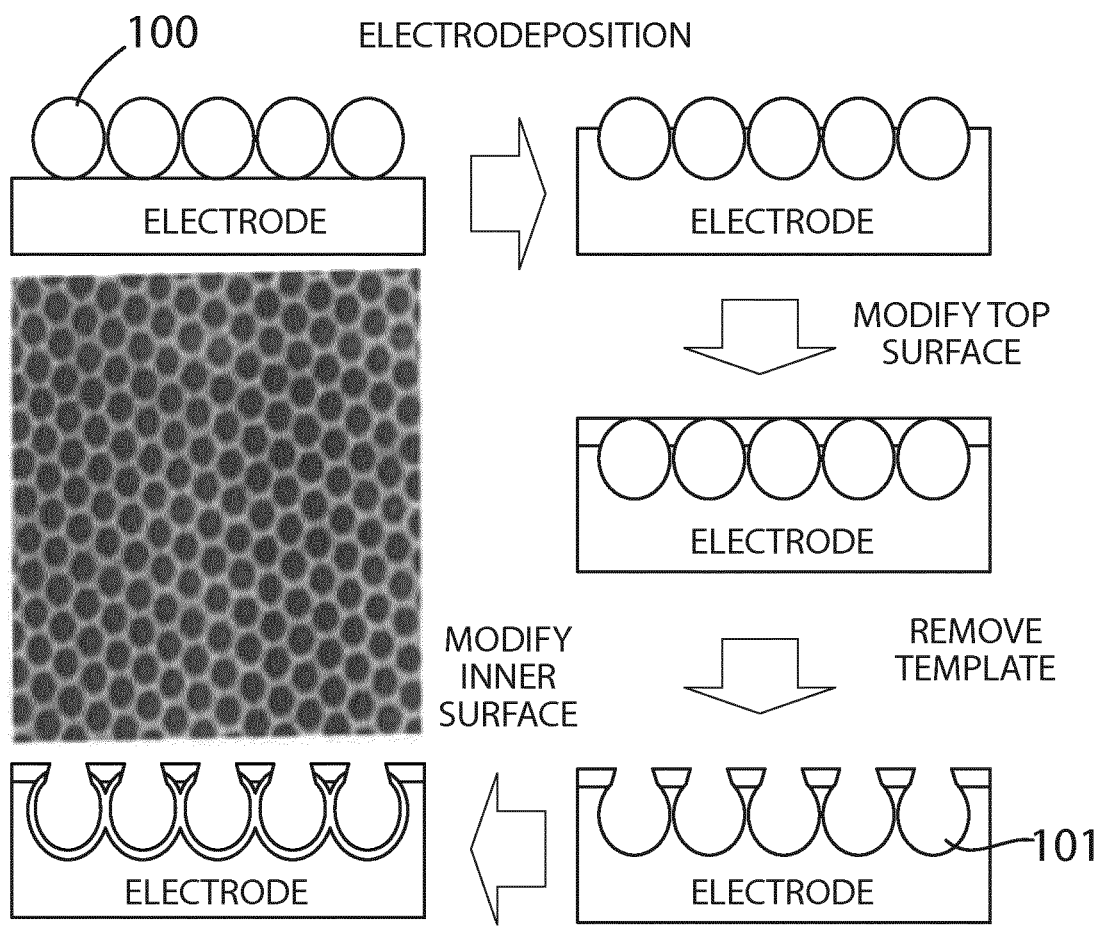
FIG. 1 shows an example of a nanosphere lithographic fabrication process for a gold microcavity array platform.

The present teaching provides a microfluidic device and method for the rapid detection of an analyte, for example, pathogens in a fluid sample. In particular, the microfluidic device described herein allows for the highly efficient capture and detection of bacterial and fungal pathogens in a fluid sample, for example a whole blood sample.

The efficiency of the device according to the present teaching at capturing and detecting an analyte as well as inhibiting deleterious non-specific adsorption is achieved through a combined effect of several features of the device. Such features include the size and shape of the chambers or cavities formed on the substrate being matched to the attributes of the target analyte. The shape and size of the cavity may be selected to match that of the target analyte. The lateral spacing of the chambers (cavities) is optimised so as to promote analyte binding while inhibiting non-specific binding. Furthermore, the capture agent may be located around the openings of, or entrances to, the chambers to promote site specific binding of the analyte across the chambers. The analyte is therefore immobilised or "locked-in". The surface coverage of the capture agent is optimised. The surface charge is also controlled so as to create an electrostatic attraction for the analyte or electrostatic repulsion of an interference.

It will be appreciated that the diameter of the chamber (cavity) and the size of the analyte will influence whether the captured analyte is bound or located across the entrance to the chamber (cavity) or inside the chamber (cavity). For example, where the diameter of the cavity is smaller than the diameter of the analyte, the analyte will bind across the cavity. In cases where the size of the cavity is larger than the size of the analyte, topography influences dominate, whereby the cells, for example, while specifically attracted to the antibody-modified surface initially, prefer to enter inside the cavity as it has a larger surface area.

Furthermore, in accordance with the device and method described herein the flow profile delivering the sample to the surface is controlled in space and time. The rate of flow of the sample across the device is controlled by the architecture of the microchannels. The geometry of the incubation chamber(s) on the disc is selected to maximise contact of the sample with the capture surface of the substrate.

These effects combine synergistically in unexpected ways and produce enhanced yields for the capture of cells compared to smooth surfaces due to a synergistic effect of the capture agents and nanostructures.

The terms chamber and cavity are used interchangeably herein to refer to the openings in the first surface (capture surface) of the substrate. The chambers or cavities form a microcavity array.

In a first implementation, the microfluidic device comprises an array of micro-cavities and is advantageously used to selectively detect gram positive, gram negative and fungal species in a fluid sample with little cross reactivity. A device according to the present teaching enables the detection of a pathogen within a fluid sample. It may enable the determination of the type of pathogen e.g. whether it is gram positive, gram negative or a fungal species, typically within a time frame of about 1 hour from depositing a sample on the device to providing an answer. The device can therefore be used in point of care diagnosis and is particularly efficient for testing patients presenting with suspected sepsis. A significant advantage is that it can detect pathogens at concentrations of <10 CFU/ml.

The microfluidic device according to a first implementation of the present teaching is described herein as a binary response device. A characteristic of the device is that it provides a yes/no indication of the presence of captured pathogens.

In a further implementation of the present teaching, the device is configured to identify a pathogen subtype and determine antibiotic resistance.

The microcavity arrays of the device according to the present teaching can be manufactured in a number of ways. Two exemplary methods of manufacture that may be used are electrodeposition and photolithography and specific examples of each of these two techniques will now be described.

1. Cavity Array Fabrication: Electrodeposition (Protocol A)

This method presents the ability to fabricate a range of ordered spherical segment metal cavity arrays in gold, other metals and conducting polymers (silver and cobalt arrays can also be produced) formed by electrodeposition via a micro- or nano-sphere lithographic fabrication process. FIG. 1 is a schematic of the nanosphere lithographic fabrication process for a gold microcavity array platform.

Polystyrene Sphere Monolayer Formation on the Gold Substrate

A 10 wt % stock solution of commercially available polystyrene (PS) latex spheres (Bangs Laboratory, USA) of the desired diameter size (25 nm to 21 µm diameter range available) are diluted to approximately 1 wt % solution in water. A thin layer of the spheres 100 is deposited onto a conductive silicon wafer coated with 1000 Å gold (Au) 525 µm thickness over a 50 Å titanium adhesion layer (Platypus Technologies, USA) and evaporated over night at room temperature.

Electrodeposition

Electrodeposition is then carried out as follows: electrolyte solutions are degassed with nitrogen for 30 minutes prior to deposition. A gold film of controlled thickness is electrochemically deposited using commercially obtained aqueous gold plating solution. A potential (V) versus an Ag/AgCl (sat. KCl) electrode is applied. With reference to FIG. 1, the thickness of the cavities 101 is easily controlled by the amount of charge (C) passed and voltage (V) applied in the electrochemical deposition step.

Selective Modification of the Array

One of the prime advantages of protocol A is the ability to selectively modify the surface. For example, using such a protocol it is possible for either the whole array to be modified with a single surface active capture agent, e.g., a cell capture antibody, or for the top surface and cavity wall interior to be selectively modified with different species. To chemically modify the whole surface following removal of the polystyrene (PS) spheres via immersion in Tetrahydrofuran (THF) for 3 hours, the whole cavity array (both top surface and cavity walls) may be immersed in a solution of the desired capture agent overnight at room temperature. Selective modification of the top surface and cavity walls with different thiols is achieved via a two-step adsorption process, presented in FIG. 1. The arrays are first immersed in a solution of one surface active ligand overnight at room temperature. The top surface modified arrays are then immersed in THF for 3 hours to remove the PS spheres followed by immersion in an alternative thiol overnight at room temperature.

It will be appreciated that this method is particularly suited for the fabrication of cell adhesion platforms in that, for example, a suitable surface active ligand can be used to tailor the surface in terms of blocking non-specific binding which provides the ability to control the positioning of adhered cells. In an alternative to this method, and as described below, it is possible to provide for mass production of optimised microcavity arrays. Different sized cavities can be readily fabricated in different regions of the device for each target pathogen size.

2. Cavity Array Mass Production: Photolithography (Protocol B)

Figure 2:
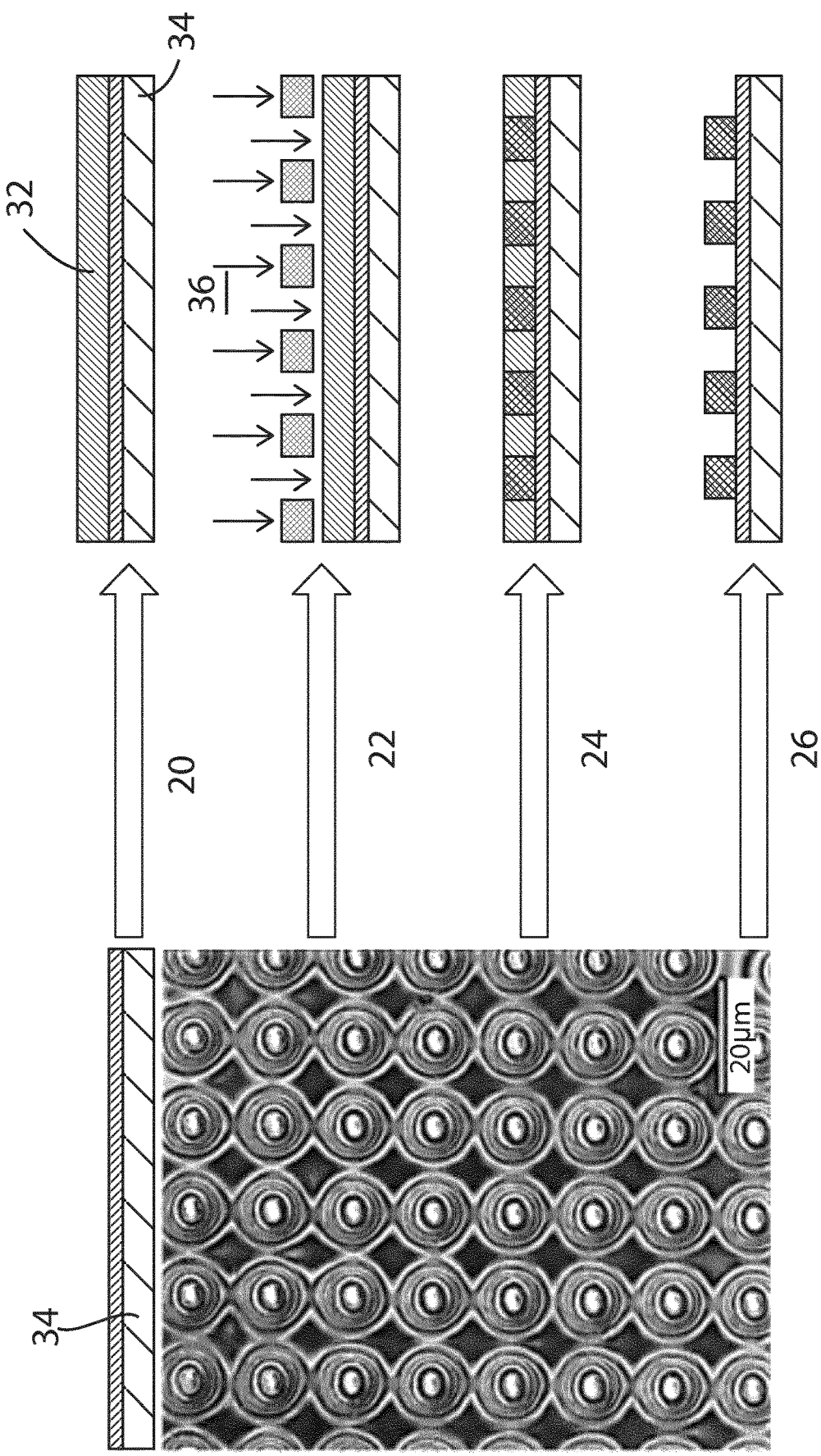
FIG. 2 is a schematic of the photolithography fabrication process for the mass production of the cavity array substrate.

FIG. 2 is a schematic of the photolithography fabrication process for mass production of the cavity array substrate.

FIG. 2 shows a scanning electron micrograph (SEM) image example of a 10 micron diameter photolithography fabricated cavity array, images were recorded using 5.00 kV accelerating voltage. The diameter can be varied easily using custom-made commercially produced masks; currently optimizing 2 micron diameter array for the microfluidic device according to the present teaching.

As shown in FIG. 2, the substrate 34, which in this example is gold coated silicon wafer, is patterned with photoresist 32. UV photolithography involves the use of ultraviolet light to pattern a surface, in this case with UV sensitive photoresist. The resist is spin-coated onto a substrate (for example, the substrate is silicon in the case of the device of the present teaching), and exposed to UV light at wavelength 365 nm through a specific photomask. The resist is then developed in an appropriate solvent, to remove non-crosslinked resist.

With reference to FIG. 2, the method involves using UV light 36 to pattern surface 34. Step 1, indicated by reference numeral 20, involves spin coating photoresist such as SU-8 3005 onto the surface of substrate 34 at 500 rpm. Step 2, indicated by reference numeral 22, involves aligning mask and exposing SU-8 3005 to 365 nm UV light 36 followed by step 3, indicated by reference numeral 24, which involves a pre-bake at 65° C. for 1 minute, followed by prebake at 95° C. for 2 minutes. The exposed areas cross-link becoming less soluble. The final step indicated by reference numeral 26, relates to the step of ultrasonic wash in developer for 1 minute whereby the unexposed areas are more soluble and wash away in developer.

The photoresist used in the method of manufacture of the device according to the present teaching is SU-8 3005, purchased from A-Gas Electronic Materials. The skilled person will appreciate that other suitable commercially available photoresists could be used. SU-8 is a negative resist, formed by dissolving SU-8 resin in an organic solvent and adding a photo-initiator. When exposed to UV radiation, the photo-initiator decomposes and forms an acid, which catalyses cross-linking in the resist. This reaction is further amplified by the application of heat, where the organic solvent evaporates from the resist. The cross-linked resist therefore becomes less soluble in the developing solvent. In short, areas exposed to UV remain on the substrate after development, and areas blocked from the light are washed away revealing the underlying gold substrate at the base of the cavity array.

Spin Coating

While a variety of different techniques may be used to provide a coating, the present inventors have concluded that spin coating is the quickest and easiest method to coat the substrate with resist. The substrate is held on a spinning vacuum chuck, and a measure of resist is deposited in the middle. The wafer is then spun at 500 rpm for ten seconds, to spread the resist evenly over the silicon, and then at higher rpm to achieve a specific film thickness.

Figure 3A:
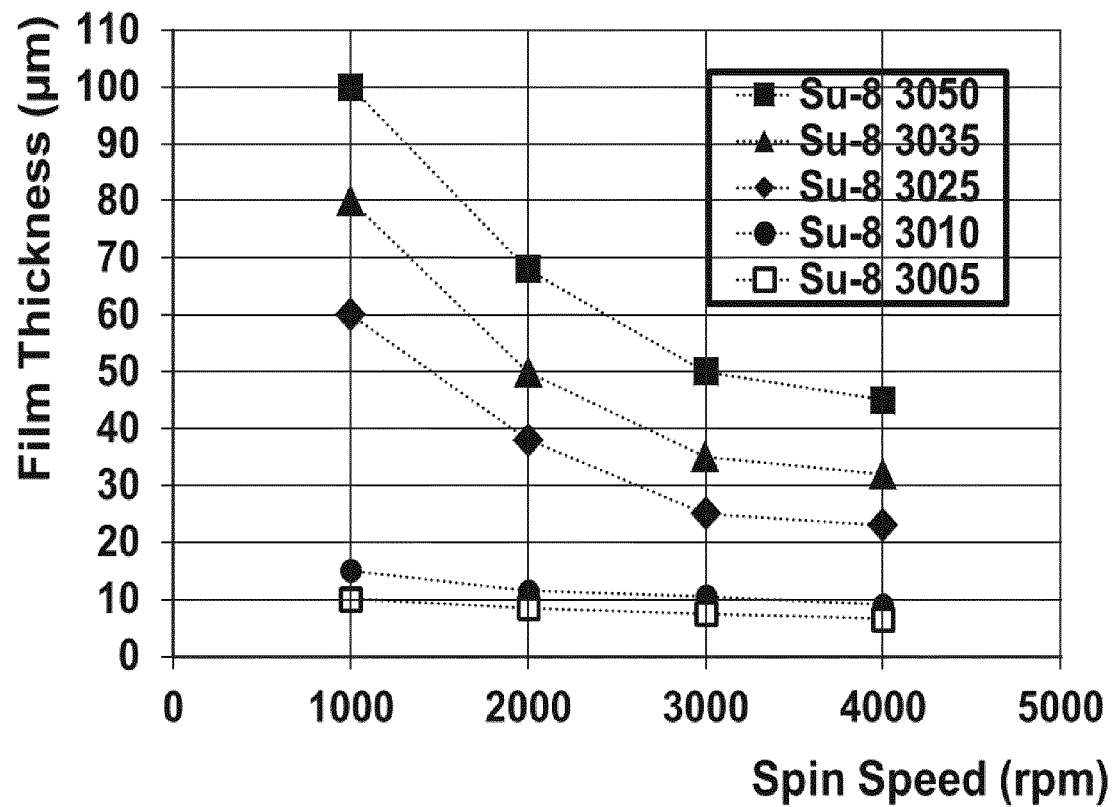
FIG. 3A is a graph showing the relationship between film thickness (µm) and spin speed (rpm) for a range of commercially available photoresist solutions.

In order to achieve 2 µm deep cavities, a 2 µm thick layer of photoresist is required. Layer thickness is determined by the spin speed in rpm, spin time, and the viscosity of the photoresist, and see FIG. 3A. The higher the viscosity of the resist, the thicker the film that can be created. As such, the present inventors used SU-8 3005, the least viscous resist of the SU-8 3000 series. It was determined that the resist should be spun in the region of 5500 to 6500 rpm, to achieve a film thickness of 2 µm.

Soft Bake

After spin coating, a soft bake is carried out. During the soft bake, a small amount of the organic solvent in the resist evaporates, causing the resist film to solidify slightly, making it more viscous. This is beneficial, especially during contact lithography, where the mask is in contact with the substrate, as residue from the resist is not left on the mask, thus increasing the lifetime of the mask.

Soft baking is generally carried out at 95° C. for 3 minutes for films under 10 µm thick. Baking at too high a temperature, or for too long, may introduce cracks and fissures into the resist film. Soft baking can be performed in a conventional oven, but can cause the solvent to evaporate from the top surface of the resist film, forming a 'skin', which prevents the underlying solvent from escaping. Therefore, it is preferable to perform the soft bake on a vacuumed hot plate, which is faster, easier to control, and promotes even evaporation of the solvent.

Exposure and Post Exposure Bake

After soft baking, the wafer is transferred to an illumination/alignment device. This device has a high magnification camera to align the wafer with the mask features with high accuracy. It will be appreciated that this is only really necessary for multi-layer lithography i.e. creating features of different heights on the same wafer. In the case of the device according to the present teaching, the cavities require only single layer lithography, and so alignment isn't as crucially important. The wafer is held on a vacuum stage, and the mask is bolted over it. The stage position is adjustable in the X, Y and Z directions, and can also be rotated to align with the mask. The stage is then moved under the UV lamp, and the mask pattern is transferred into the photoresist.

Optimum wavelengths for photolithography range from the deep UV (150-300 nm) to near UV (350-500 nm), depending on the application and the resist used. SU-8 is most commonly exposed between 350 and 400 nm, with 365 nm (i-line) being the optimum wavelength. For film thicknesses under 10 µm, the optimum exposure energy is 100-200 mJ/cm$^2$. The adhesion strength of the resist varies depending on the substrate used. SU-8 has relatively poor adhesion strength on gold, and requires higher exposure doses. In the case of the present teaching the resist is exposed for 10 seconds on silicon wafers, and for 20 to 25 seconds on gold wafers.

As mentioned earlier, the UV radiation causes the photo initiator in the resist to decompose to hexafluoroantimonic acid, which causes cross-linking reactions in the exposed regions of the resist. While these reactions take place at room temperature, the reaction rate is greatly increased with heat. Typical post exposure bake temperatures range from 60-100° C. Longer bakes at lower temperatures are more beneficial, as rapid temperature jumps can cause thermal stresses and cracks in the resist. In the case of the method of manufacture for the device according to the present teaching, the post exposure bake is generally carried out at 65° C. for 1 minute, followed by 2 minutes at 95° C. As the cross linking is completed, an image of the mask features appears in the resist during the post exposure bake.

Development

Development is the dissolution and removal of the un-crosslinked resist, to leave the desired topography. In the method of manufacture for the device according to the present teaching 'wet' development is used, which involves submerging the resist in developer solvent. The solvent used herein is MicroPosit EC Solvent (2-methoxy-1-methylethyl acetate). This method relies on the differences in molecular weight between the crosslinked and the un-crosslinked resist. Unexposed, and therefore un-crosslinked regions of the resist are washed away. The liquid is kept in constant agitation, in order to continually feed fresh developer over the resist, and to remove resist from small cavities or channels. The process is greatly aided by the use of a sonic bath, or by placing on an oscillating platform. Typically, the cavities are developed for 1-3 minutes, usually in a sonic bath. After development, the finished wafer is cleaned with isopropanol and deionised water, and dried with nitrogen.

Hard Bake

The final (and optional) stage is a hard bake. This is to remove any residual organic solvent in the resist, and to anneal the resist surface which may have been weakened during development. The glass transition temperature of fully crosslinked SU-8 is in the region of 200° C. Accordingly, hard baking can be carried out at higher temperatures. In accordance with the method described herein, the wafers may be hard baked at 150° C., for 10 to 15 minutes. Hard baking is not so important for one-use electrode cavities, but for wafers being used for casting or embossing, where structural integrity and wafer lifetime are important, a hard bake is critical.

Figure 3B:
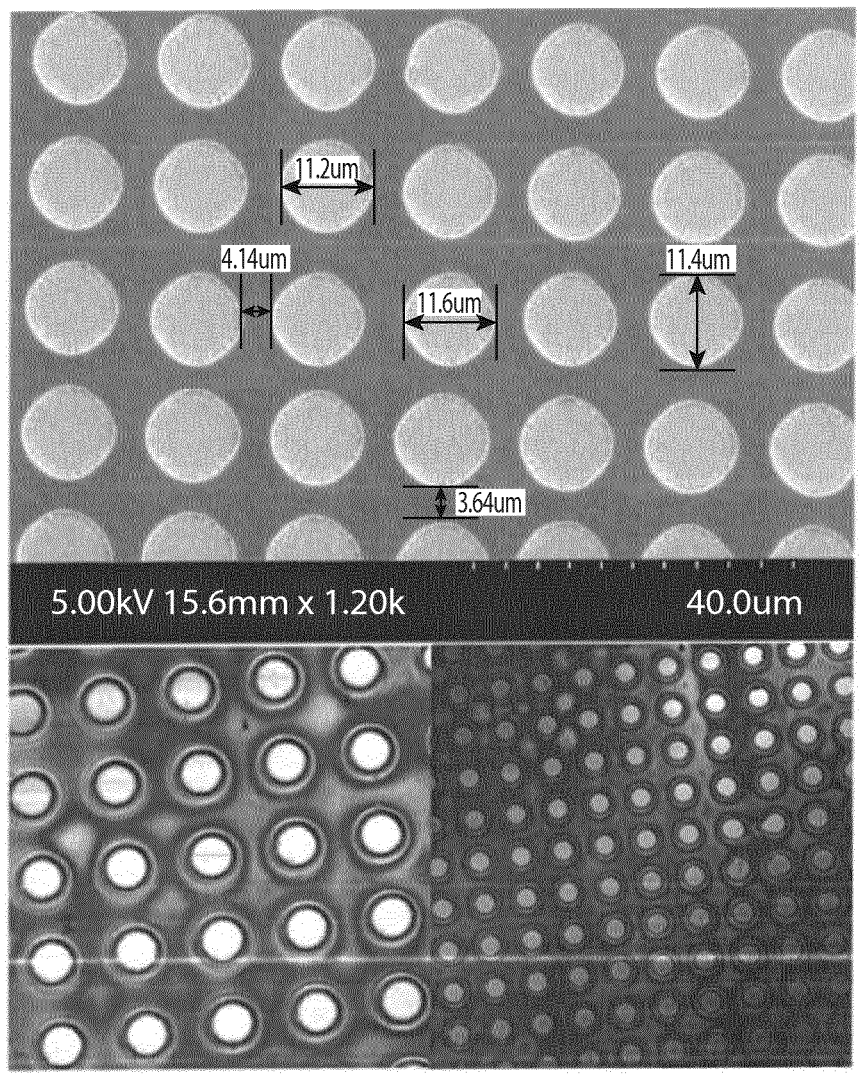
FIG. 3B shows SEM and confocal images of gold cavities mass produced by photolithography.
Figure 3C:
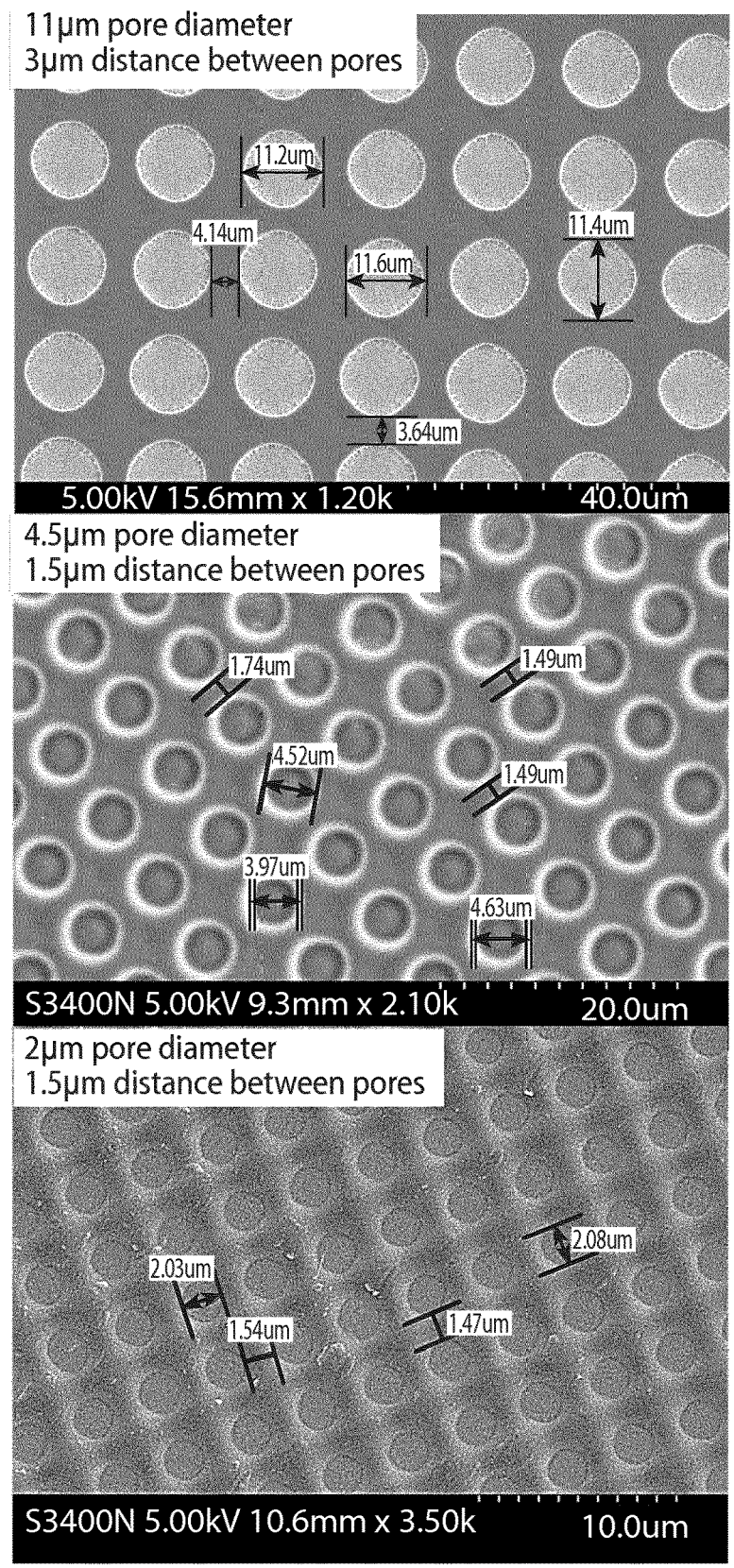
FIG. 3C shows SEM images of cavities produced by photolithography with varying cavity pore diameter to show fine tuning of the array to capture different analytes (for example, cell 5-20 µm in size and bacteria 1-5 µm in size)

With reference to FIG. 3B, the resulting array presents photoresist at the top surface and gold at the base of the cavity which allows the array to be electrochemically addressed.

3. Modification of the Cavity Array Surface

The capture antibodies or capture protein may be immobilised on the first planar surface by means of stamping onto said planar surface. The top surface of the array (first planar surface of the substrate) can be modified by stamping with capture antibodies or capture protein. For example, the top surface of the array can be stamped with gram positive antibody, gram negative antibody or yeast protein or an antibody that selectively captures a pathogen sub-type.

As the top surface of the array is not gold in this example, microcontact printing (μCP) is employed to modify the top surface of the array (via antibody adsorption). μCP is a form of soft lithography that uses the relief patterns on a master polydimethylsiloxane (PDMS) stamp to form patterns on the surface of a substrate through conformal contacts. It will be appreciated by the person skilled in the art that other suitable stamping materials could be used.

Preparing the Master

The master is prepared using the photolithography technique. The master is created on silicon. Photoresist is applied to the surface (500 rpm initially for 10 seconds then increased to 1000 rpm for 30 seconds) and patterned by a photomask and UV light. The master is then baked (95° C. for 3 minutes), developed (2 minutes with sonication) and cleaned before use. The photoresist is very stable and the wafer master can be reused numerous times as a topographic template for the stamp.

Creating the PDMS Stamp

Figure 4A:
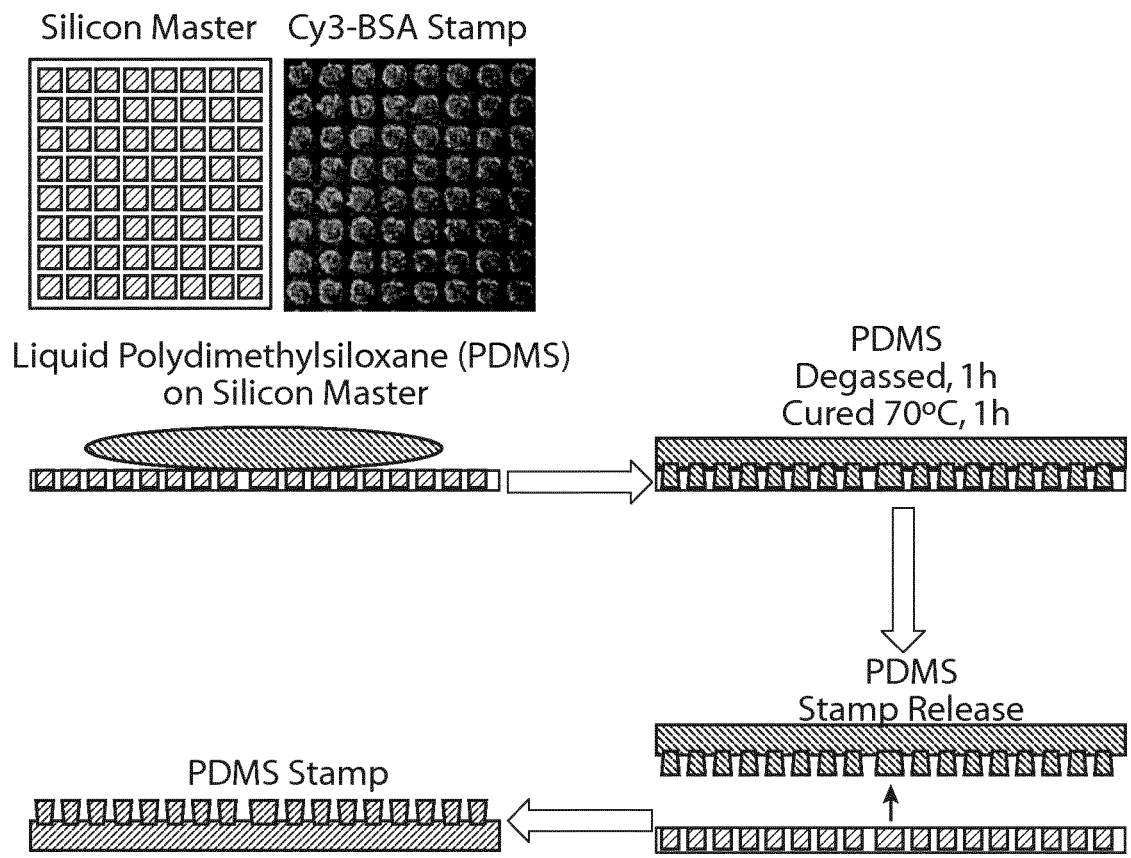
FIG. 4A is a schematic of the fabrication process for the polydimethylsiloxane (PDMS) stamp used to modify the top surface of the photoresist cavity array; Confocal image example of Cy3-labelled BSA (Bovine Serum Albumin) stamped onto a glass substrate using the PDMS stamp (10×10 µm squares with 5 µm distance between each square); the luminescence image was recorded using a 40× oil immersion objective lens (NA 1.4) with 540 nm HeNe laser excitation.

A schematic for the fabrication process of the PDMS stamp used to modify the top surface of the photoresist cavity array is presented in FIG. 4A. After fabrication, the master is placed in a petri dish and PDMS poured over the master at a 10:1 ratio of silicone elastomer and a silicone elastomer curing agent. This mixture consists of a short hydrosilane crosslinker that contains a catalyst made from a platinum complex. After pouring, the PDMS is placed under vacuum for 1 hour and then cured at 70° C. for 1 hour to solidify the polymer. The stamp is then peeled off and cut to the desired size. The stamp replicates the opposite of the master. Elevated regions of the stamp correspond to indented regions of the master.

Surface Modification: Antibody Stamping

The desired antibody (100 μg/ml stock concentration) is placed in contact with the PDMS stamp for 15 minutes at room temperature. Suitable antibodies for use include GTX40307 Gram Negative Endotoxin [308] Mouse Monoclonal Antibody, GTX36804 Gram positive bacteria LTA [3801] Mouse Monoclonal Antibody and Native *Candida Rugose* Cholesterol Esterase Purified Protein. The antibody solution is removed and the stamp with adsorbed antibody and excess solution removed with a nitrogen stream. The antibody adsorbed stamp is then placed onto the photolithography array surface and pressed lightly to ensure adequate contact occurs between the surface and stamp. The stamp is incubated with the array for 15 minutes at room temperature. The stamp is peeled away from the surface and antibody is now adsorbed onto the top surface of the cavity array substrate. The exposed gold at the base of the cavity array may be modified with a thiol of choice. Where thiol modification is not required, the gold is blocked with thiolated PEG (polyethylene glycol) to reduce non-specific binding. The antibody modified array is incubated with a 1 mM solution of thiolated $PEG_8$-COOH overnight at room temperature. Finally, the whole array is incubated with a 1% BSA (bovine serum albumin) solution for 1 hour at room temperature to inhibit any remaining potential non-specific adhesion to the surface. The array is then inserted into the binary response device for bacteria capture and electrochemical detection.

Figure 4B:
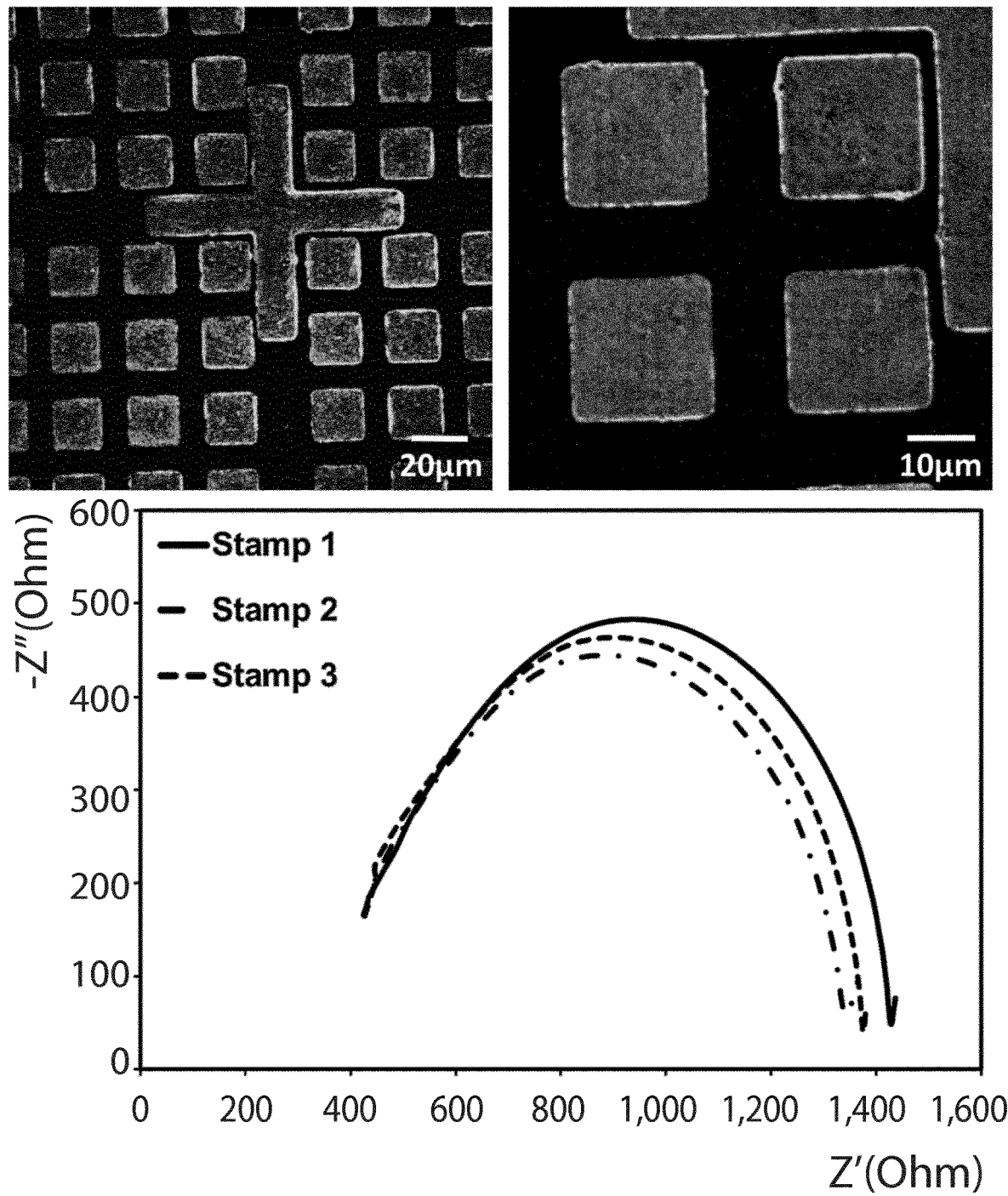
FIG. 4B shows confocal images of an antibody stamped planar electrode surface (Top) and impedance spectra of 3 independently Gram negative antibody stamped electrodes showing reproducibility of the AB stamp.

With reference to FIG. 4B, confocal images of the capture antibodies immobilised on the first surface by means of stamping onto said planar surface showed reproducible impedance spectra of 3 independently Gram negative antibody stamped planar electrodes within the microfluidic device.

Figure 4C:
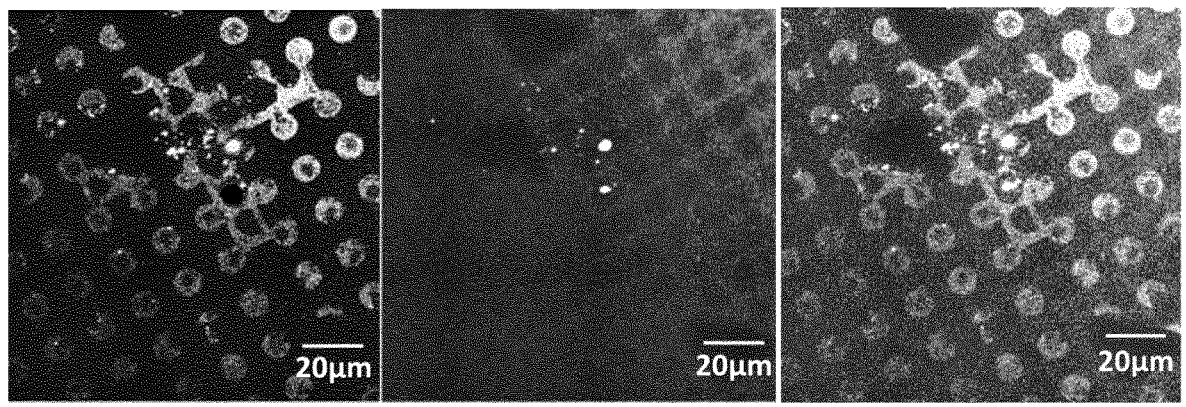
FIG. 4C shows confocal image example of Cy3-labelled BSA stamped onto a photolithography cavity array substrate surface using a PDMS stamp. The luminescence image was recorded using a 40× oil immersion objective lens (NA 1.4) with 540 nm HeNe laser excitation.
Figure 4D:
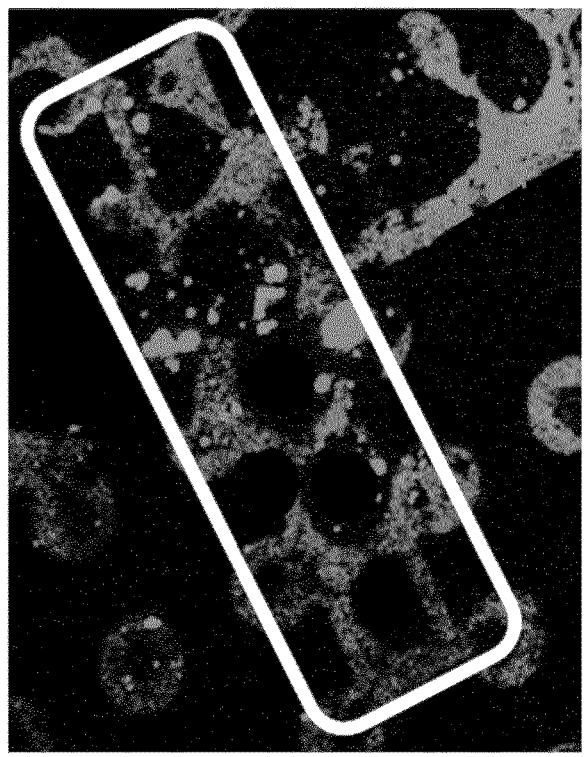
FIG. 4D shows a confocal image showing the cavity array pores clearly visible and Cy3-labelled BSA moulds around the pore opening confirming successful stamping.

The top surface of the cavity array can also be modified by stamping with capture antibodies or capture protein and a confocal image of the stamp with Gram negative antibodies immobilised on a cavity array (produced by photolithography) is shown in FIGS. 4C and D.

The microfluidic device such as described herein can be used as a binary response device or as a multiplex device. The binary response device provides an indication of the presence or otherwise of an analyte; that is, a "yes/no" binary response, in a sample, for example a whole blood sample. The multiplex device as described herein provides the capability of detecting the particular type of analyte. The multiplex device can be used following an initial diagnosis of the type of pathogen (e.g. gram positive, gram negative or a yeast pathogen). It provides more granular or detailed information on a subtype of analyte.

4. Binary Response Device Centrifugal Platform Protocol

General Disc Design

The design of the Binary response disc is carried out using the SolidWorks Premium 2015 program. This is a solid modelling computer aided design (CAD) program. A 3D model of the disc is initially drawn. Different depths of the disc's features lie at different depths within the model structure. Overall, nine different layers are extracted from the model design. Each layer must be opened in another CAD program labelled AutoCAD. Here, each of the polylines is converted to continuous lines for an ease of fabrication at a later stage. Each layer is then saved as a DXF file.

In one configuration the substrate may be fabricated from one or more layers of Poly(methyl methacrylate) (PMMA). Where a plurality of layers is provided, a base layer of PMMA may be fabricated so as to receive and locate working gold electrodes. Other PMMA layers may be coupled to this base layer to form the ultimate multilayer structure.

5. Binary Response Device

Figure 5A:
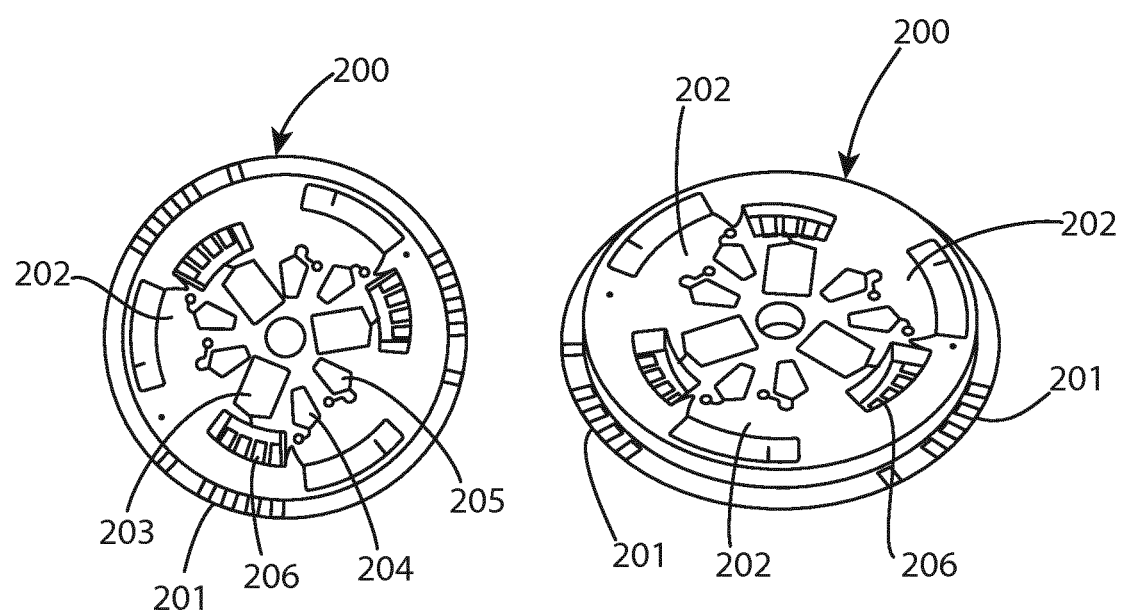
FIG. 5A shows images of the Binary response device according to one aspect of the present teaching with inserted electrodes for bacteria capture and detection.

FIG. 5A shows images of an example of a binary response characteristic device 200 with inserted electrodes 201 for bacteria capture and detection.

The Binary response disc 200 in this exemplary arrangement contains three separate testing sites 202. The structure is mirrored to allow for the sites to be completely identical. The site contains a sample reservoir 203, wash step reservoir 204 and a PBS reservoir 205. Vents are located at the top of the reservoirs to allow for ease of loading of the device.

Figure 6:
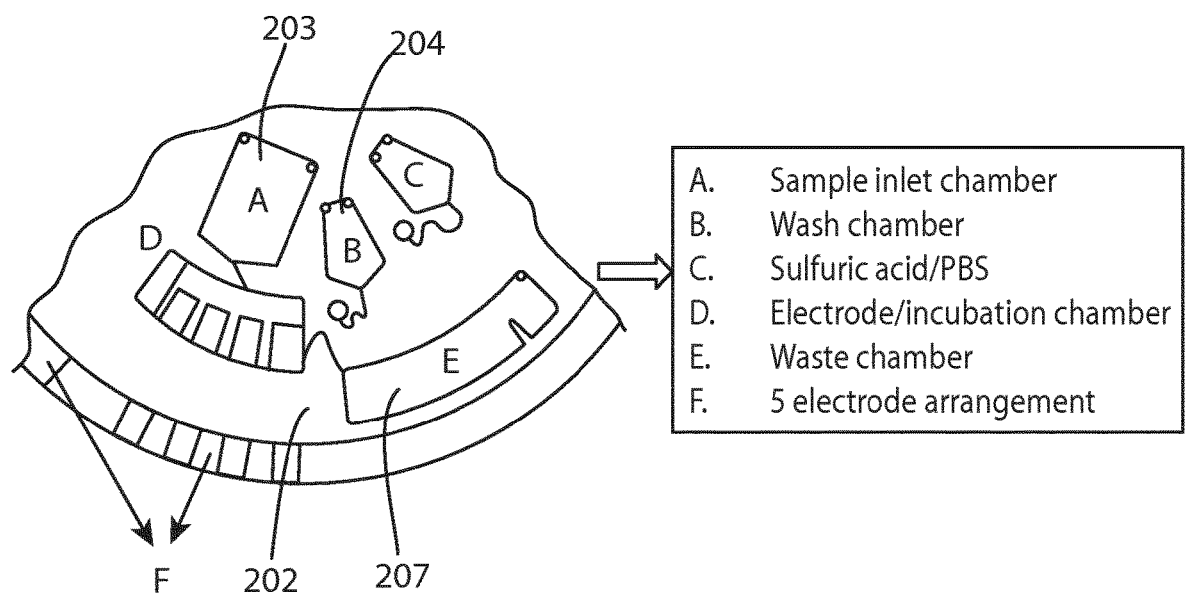
FIG. 6 shows a labelled testing site on the Binary response device of FIG. 5A.

A labelled testing site 202 on the binary response device is presented in FIG. 6. The electrode structure within the incubation/electrode chamber is as follows:
  ITO/Gold Electrode (reference)
  Gram Positive (working electrode)
  Gram Negative (working electrode)
  Yeast (working electrode)
  Counter electrode It will be appreciated that the antibodies may be placed in any order provided the arrangement in all circumstances is as follows: (Left) Reference electrode, (centre) Working electrode and (right) Counter electrode.

It will also be appreciated that other metals and conducting polymers may be used as counter or references (examples include but are not limited to silver, carbon and silicon).

The following is an example of a method of capturing and detecting an analyte using the microfluidic device according to the present teaching.

With reference to FIGS. 5A, 5B and 6, a 2 ml whole blood sample is loaded into sample inlet chamber 203 (Chamber A). The sample flows down directly into the electrode chamber 206 (Chamber D) via a simple microchannel. A spin rate of 10 Hz is applied to the device to slowly displace the liquid into the electrode chamber. Simple siphon technology is implemented here to contain the sample within the incubation chamber for a defined time period. The incubation time used for the device according to the present teaching is between approximately 7-10 minutes. Once the device according to this aspect of the present teaching is slowed down to 4 Hz the sample primes the siphon by capillary action. The disc's angular frequency is increased to allow the liquid to travel to the waste chamber 207 (Chamber E), located to the right of the electrode chamber 206. The disc is then set to a frequency of 30 Hz. This triggers the wash step (Chamber B) by bursting the dissolvable film (DF) tab located in the wash step microchannel into the electrode chamber 206 (Chamber D) which can immediately be displaced into the waste chamber. The spin rate here is reduced to 10 Hz. The wash buffer overflows into the second section of the waste chamber 207 where it will burst the waste chamber DF tab. This relieves the lower channel's air pressure and puts the DF tab into a burstable state. The device is then spun at a frequency of 30 Hz which drives the PBS (phosphate buffered saline solution) (Chamber C) into the electrode chamber 206 (Chamber D) where it will remain for further testing purposes. The device (disk) is removed from the spin stand mechanism where it is then attached to a potentiostat for detection. This step can be integrated into the spin stand.

Figure 7A:
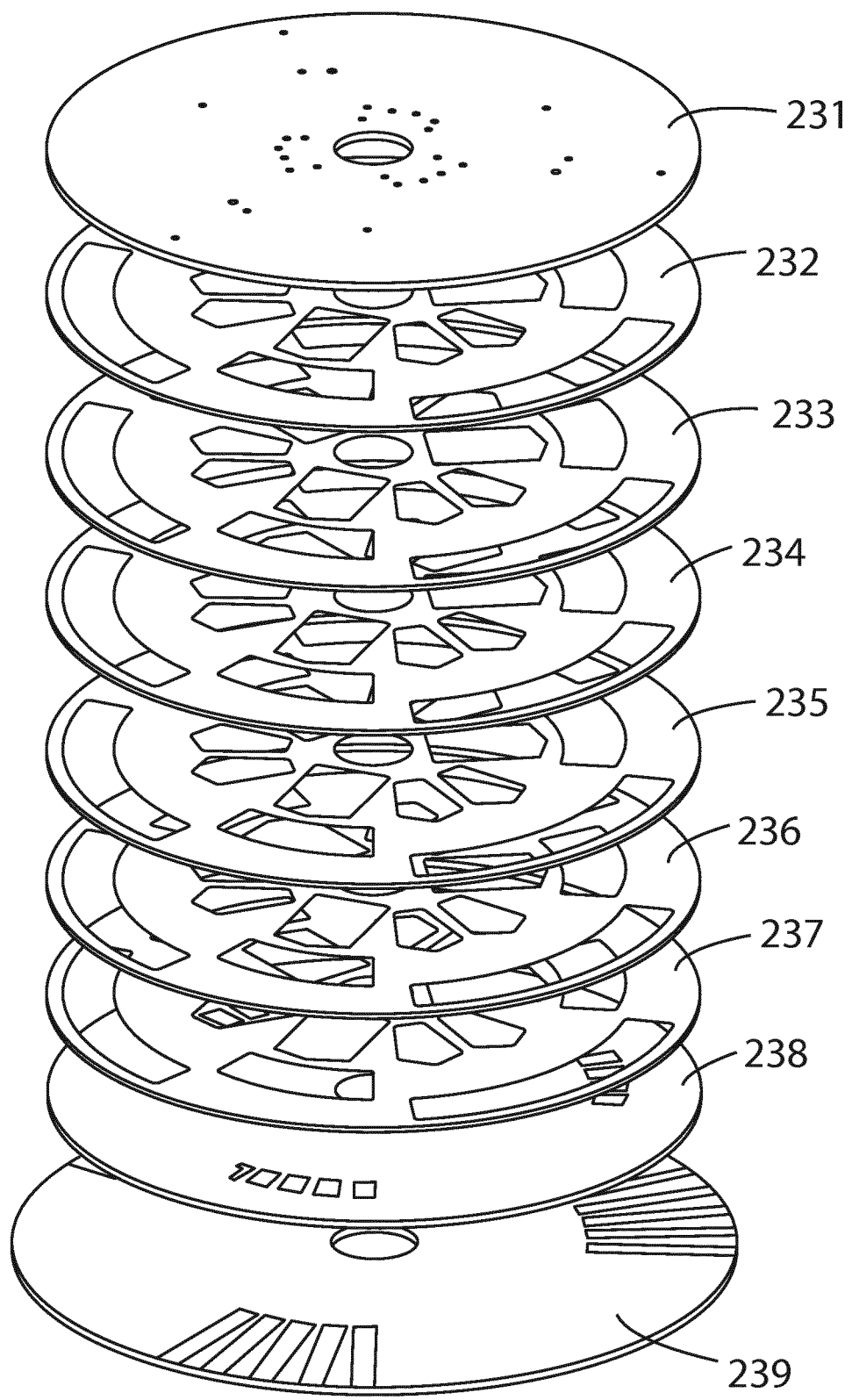
FIG. 7A is an exploded 3D view showing the composition of a binary response device according to an alternative aspect of the present teaching showing the layers which make up the device.

FIGS. 7A to 7D show another example of a binary response device 200 according to the present teaching. Although reference numeral 200 has been used to refer to this binary response device, it will be appreciated that it is a different device to that of FIG. 5A. In particular there is a difference in the location of the wash solution chamber 604 and the electrolyte solution chamber 605 as compared to the wash chamber 204 and the electrolyte chamber 205 of the device shown in FIG. 5A for example. The wash step and the electrolyte step of the method according to the present teaching are controlled by the spin rate. This will be discussed further below with reference to FIG. 7D. With reference to FIG. 7B the same reference numerals have been used to indicate the same components of the device shown in FIG. 5A.

Figure 7C:
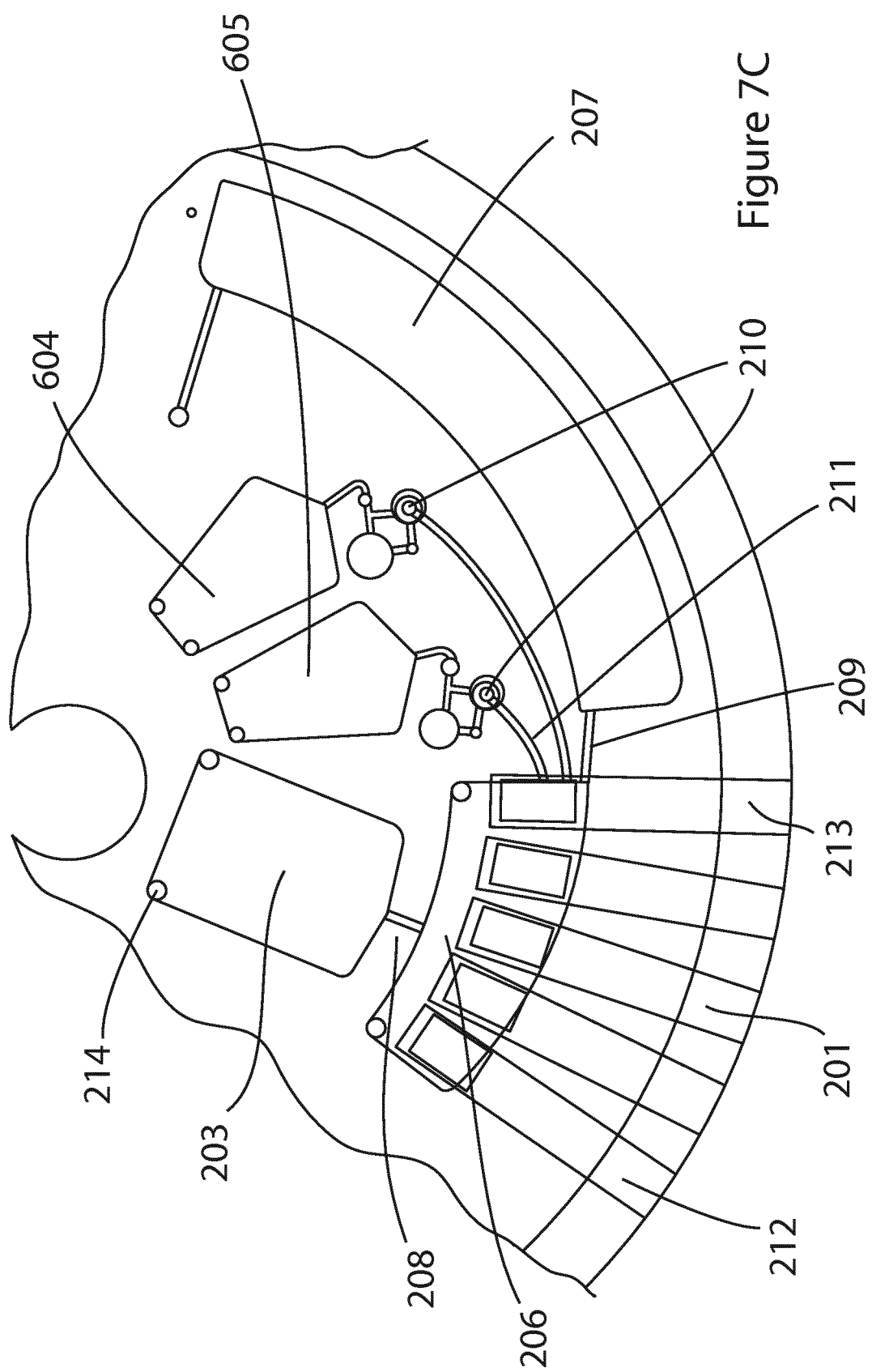
FIG. 7C shows a 2D schematic of one of three identical testing sites of the device shown in FIG. 7B.

The design of the device shown in FIGS. 7A to 7C is carried out utilizing SolidWorks Premium (2015 Edition). For the purpose of the design, the model was created in 3D assembly mode for ease of extraction of the nine 2D layers in the device. Individual layers are saved as .DXF files and are each altered within a secondary Computer Aided Design (CAD) software, AutoCAD. AutoCAD provides additional design options for further design of the layers. Extracted 2D .DXF files comprise of a series of polyline structures which must be joined using PEDIT options within the software for ease of fabrication. The .DXF file is re-saved as an AutoCAD R12/LT2 DXF (.DXF) file.

FIG. 7A shows an exploded view of the device of FIG. 7B. Each layer has a specific function for the operation of the device.

The first layer 231 of the device is comprised of PMMA containing an array of holes acting as entry points for loading samples and reagents into the lower layers of the device. These holes are also used as venting mechanisms to ensure fluid flow throughout the system.

The second layer 232 of the device contains an assortment of microchannels necessary for the routing of liquid between specific reservoirs. These microchannels also act as a means of flow control, where channels are connected to air and pressure chambers. The height of the microchannels is is provided by the Pressure Sensitive Adhesive (PSA).

The third layer 233 of the device is comprised of 2 mm PMMA which has an assortment of reservoirs which are required for the storage of the sample, reagents and the waste. This layer also gives depth to the device which is needed for the volume of liquids used.

The fourth layer 234 is a secondary PSA layer which contains access points to the dissolvable film (DF) tab once routing of the liquid to their position is activated. This layer also contains air passages needed for air circulation and air compression to aid the control of burst frequency desired for the DF tabs.

The fifth layer 235 is mirrored against layer 4, where the only difference lies with a section for the DF tab placement and securement.

The sixth layer 236 of the device is the third PMMA layer which contains reservoirs for storage of the sample, reagent and waste. Once activated, this layer provides passage for liquid travelling from the microchannels, through the DF tab towards lower channels.

The seventh layer 237 contains microchannels for the displacement of liquid from the reagent storage chambers to the detection chamber, and finally the waste chamber.

The eighth layer 238 of the device is a PSA layer which only exposes the functionalised area of the electrodes whilst also exposes the top of the counter and reference electrodes which is vital for impedance detection within the device.

The ninth layer 239 of the device is the final section of the device which contains 3 sets of the 5 electrode configuration. These functionalised electrodes act as both the capture site for pathogens as well as a site for impedance detection.

An overview of an example of the device 200 is shown in FIG. 7B showing each individual component of a testing site 202. FIG. 7B also shows the location of functionalised electrodes 201 which are required for bacterial capture and detection.

The binary response disc 200 in this exemplary arrangement contains three separate testing sites 202. These structures are a triplicate circular pattern for a mirrored response during testing. The device 200 encloses five main reservoir sections for fluid containment. Each site contains a sample chamber 203, detection chamber 206, a wash-solution chamber 604, an electrolyte solution chamber 605 and a waste reservoir 207.

FIG. 7C shows an overview of an individual testing site contained within the binary response device 200 and shows each individual component required for the automation of the mechanisms present within the testing sites 202. The 5 gold electrode arrangement located on layer 9, 239, of the device are as follows:

Reference Electrode 212
Gram Positive Electrode 201
Gram Negative Electrode 201
Fungal/Yeast Electrode 201
Counter Electrode 213

It will be appreciated that the antibodies may be placed in any order provided the arrangement in all circumstances is as follows:

(Left) Reference electrode, (centre) Working electrode and (right) Counter electrode.

Vents 214 are located at the top of each reservoir section for ease of loading samples and reagents whilst allowing the displacement of air within the device for ease of flow for each fluidic component. This venting system allows ease of loading of the sample into sample chamber 203, wash-solution chamber 604 and electrolyte-solution chamber 605.

With reference to FIGS. 7A and 7C, the microchannel 208 located on layer 3, 233, of the device connects sample chamber 203 to the detection chamber 206 and has a constant width and depth. A secondary microchannel 209 located on layer 7, 237, of the device connects detection chamber 206 to waste chamber 207. Channel 209 has a constant width and a varied depth for fresh whole blood samples and samples placed in buffer.

DF (dissolvable film) tabs 210 are located beneath their corresponding reservoirs (or chambers). These tabs are located on layer 5, 235, of the device 200 and are positioned above channels 211, found on layer 7, 237. Channels 211 allow for full dislocation of liquids from reservoirs 604 and 605 to chamber 206 once the corresponding DF tabs have been actuated.

Figure 7D:
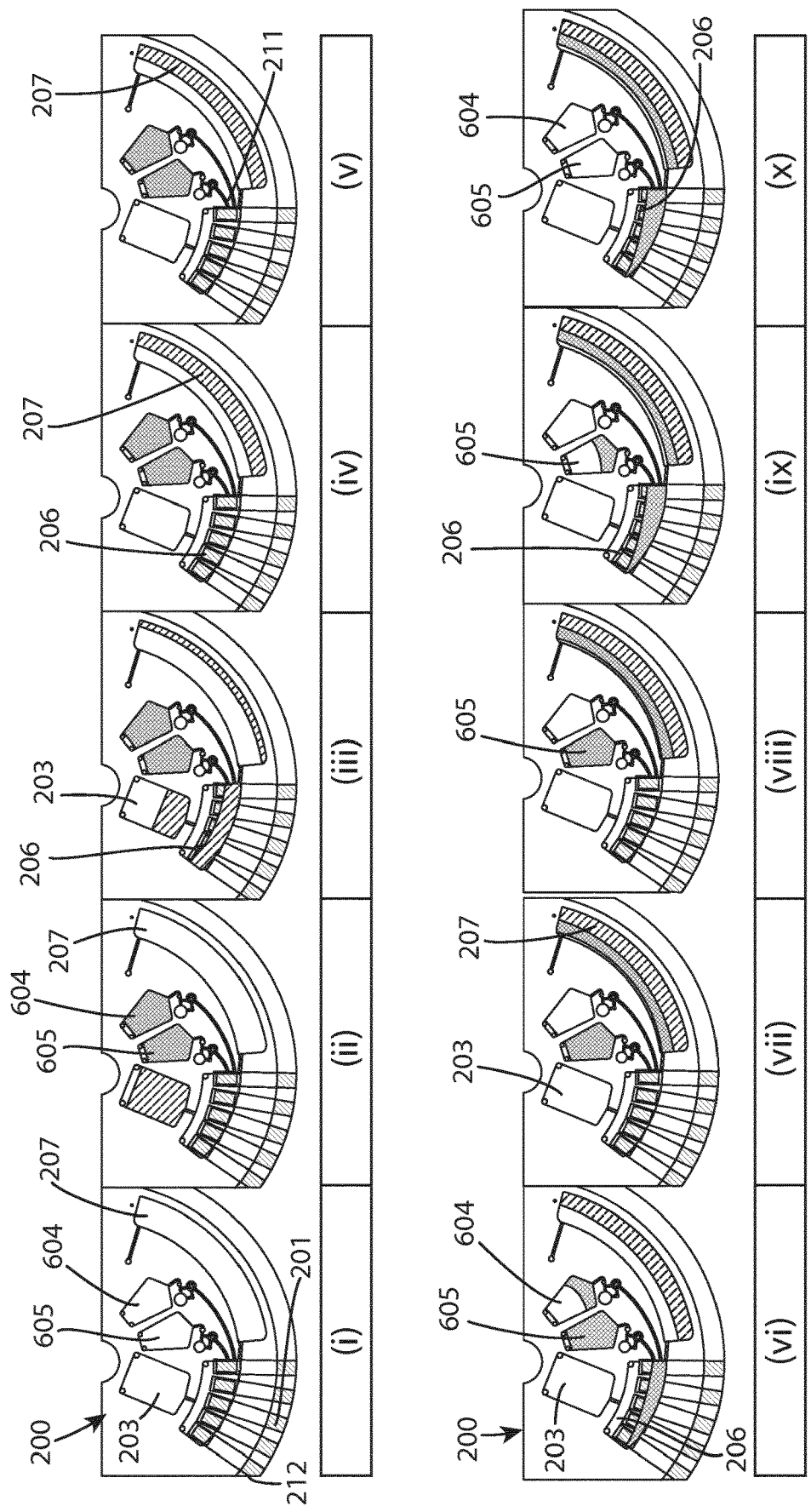
FIG. 7D (i) to (x) is a schematic showing the sequence of events of the method according to the invention where (i) demonstrates the chamber in a pre-loaded state, (ii) shows loading of fresh whole-blood sample and reagents, (iii) shows passing of sample into the detection chamber, and continuation of sample flow into the waste chamber, (iv) shows full displacement of blood into the waste chamber; (v) shows where wash step valve is put into a burstable state due to an increase in the angular velocity, (vi) shows displacement of wash-solution from wash-chamber to detection chamber via a channel on the $7^{th}$ layer of the device, (vii) shows full displacement of wash-solution to waste chamber, (vii) a further increase in the angular velocity puts electrolyte valve in a burstable state, (ix) shows displacement of electrolyte solution from wash-chamber to detection chamber via a channel on the $7^{th}$ layer of the device; and (x) shows full displacement of electrolyte solution into detection chamber.

FIG. 7D demonstrates the operation of capturing and detecting an analyte using the microfluidic device according to the present teaching. With reference to FIG. 7C and FIG. 7D, a whole blood sample is loaded directly into sample chamber 203 via vents 214. The wash and electrolyte solutions are pre-loaded in chambers 604 and 605 respectively. FIG. 7D(iii) demonstrates the flow of the whole blood sample from sample chamber 203 to detection chamber 206. A spin frequency is applied to the system in a counter-clockwise motion forcing the sample through microchannel 208 due to the outward applied centrifugal force. The hydrophobic nature of the PMMA sample reservoir and hydrophilic channel 208 promotes flow in the outward direction into the detection chamber 206. The viscous nature of the sample entering the detection chamber allows for a build-up of the sample over the detection electrode arrangement 212, 201, 213. In parallel to the fast accumulation of the sample in detection chamber 206, the sample displaced into the waste chamber 207 is one slow, continuous flow.

FIG. 7D shows the full dislocation of the whole blood sample under spin frequency. Once this is achieved the system's angular velocity ω is increased as portrayed in FIG. 7D(v). An increase in ω forces liquid from wash-solution chamber 604 through channels connecting to the exposed top section of the DF (dissolvable film) tab. Once wetted, the DF tabs are in a burstable state and will dissolve in 20-30 seconds. It has been determined that the positioning of the DF tab is critical in the optimisation of the burst frequency, where radial positioning, surrounding air volume sizes, and lower channel lengths must be considered.

Wash solution is relocated from chamber 604 to detection chamber 206 via a lower channel as shown in FIG. 7D(vi) at a constant spin frequency. This solution washes over electrodes found in the detection chamber and removes uncaptured particles and residual sample components. The applied centrifugal force completely relocates all fluid into waste chamber 207 as shown in FIG. 7D(vii) and the liquid level within the waste chamber reaches a critical volume and now blocks the lower waste channel 209.

FIG. 7D(viii) shows the final increment of the angular velocity ω on the system. A higher frequency triggers the second DF tab 210 within the system. Once actuated, the electrolyte solution flows directly into the detection chamber 206 via a lower channel 211 as shown in FIG. 7D(ix). FIG. 7D(x) portrays the final stage of the sample test, where the electrolyte solution remains in the detection chamber for the final stage analysis. The external sections of the electrodes are connected to a potentiostat for impedance detection of the analyte.

6. Multiplex Device: Type A

Figure 8:
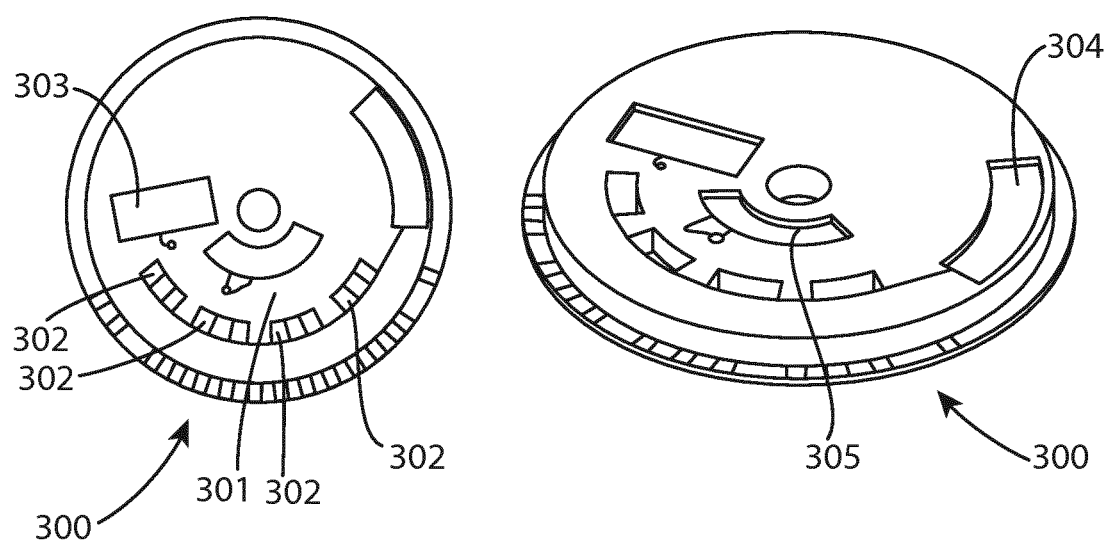
FIG. 8 shows images of the MultiPlex device with inserted electrodes for bacteria capture and detection.

In a modification to the device herein before described, a detection system comprising a plurality of chambers that can be blocked by different analytes may be provided. Such an arrangement may be provided by surface treating different regions of the detection system so as to selectively target different analytes. In this way, a first predetermined location on the disc will include a plurality of chambers that will be blocked by a first set of analytes but not by a second set. Correspondingly, a different predetermined location on the disc will be blocked by a second set of analytes but not by the first set. Such a device may be considered a multiplex device 300 and an example is shown in FIGS. 8 and 9.

In these examples the device 300 is comprised solely of one testing area 301. This device consists of 4 distinct electrode incubation chambers 302. Each incubation chamber 302 is functionalized with a specific capture antibody. Use of such a multiplex device 300 advantageously follows an initial diagnosis, for example a bacteria diagnosis from a Binary response type device (Gram positive, Gram negative or yeast determination) as described above. Using the discrimination offered by the multiplex device provides the capability of determining the specifics of the bacteria sub-species for either Gram positive or Gram negative pathogen containing sample.

For example, a 2 ml whole blood sample is loaded into the blood chamber 303. The blood is loaded and a spin rate applied. The blood separation can take from 6-9 minutes to separate. Once ready, the spin rate of the disc is increased to wet and break the blood separation chamber's DF tab. The spin rate is reduced to allow the plasma to fill up each of the chambers and allow for a slow steady flow through the four electrode incubation chambers 302. A long microchannel connects the final electrode chamber to the waste chamber 304. The flow rate of the plasma into the waste chamber is controlled using a known width of channel. Increasing the size of this channel increases the exit flow rate of the sample. The incubation time varies from 7-9 minutes. A DF tab is located in the waste chamber. Once burst, the lower-channel air pressure is released and the wash chamber's DF tab is now in a burstable state. The spin rate is increased to burst the wash buffer reservoir 305 located directly above the electrode chambers. A series of lower channels links the wash buffer reservoir 305 to the electrode chambers 302. The spin rate is reduced and the wash buffer flows through each of the electrode chambers into the waste chamber 304. The device is removed from the spin stand mechanism where it is then attached to a potentiostat for analysis.

Figure 9:
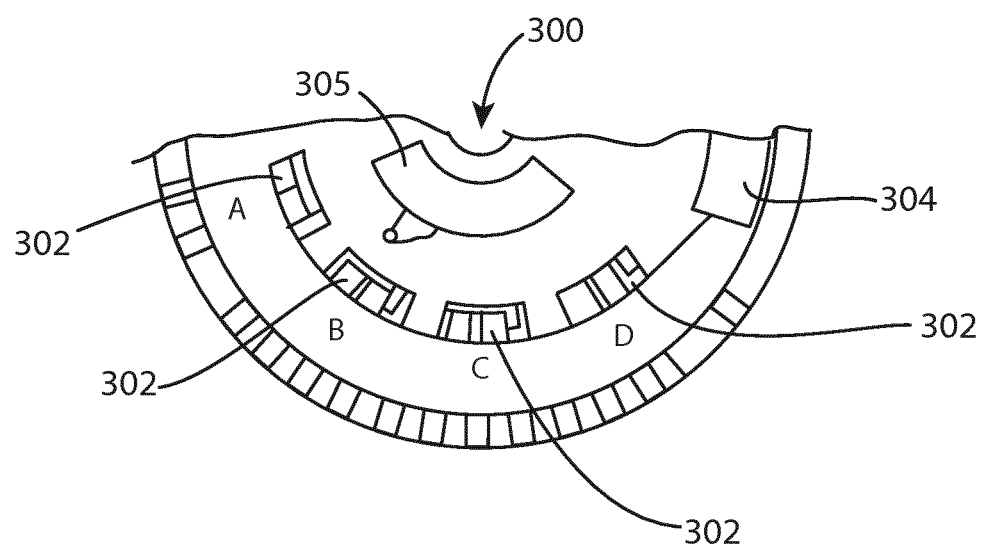
FIG. 9 shows the labelled testing site on the MultiPlex device with inserted electrodes for bacteria capture and detection.

With reference to FIG. 9, the four incubation chambers 302 are functionalised with the following for testing purposes:

A: Working electrode: antibody of choice
B: Working electrode: antibody of choice
C: Working electrode: antibody of choice
D: Working electrode: antibody of choice The arrangement in all circumstances is as follows:
(Left) Reference electrode, (centre) Working electrode and (right) Counter electrode.

7. Multiplex Stage 2 Device: Type B

Figure 10:
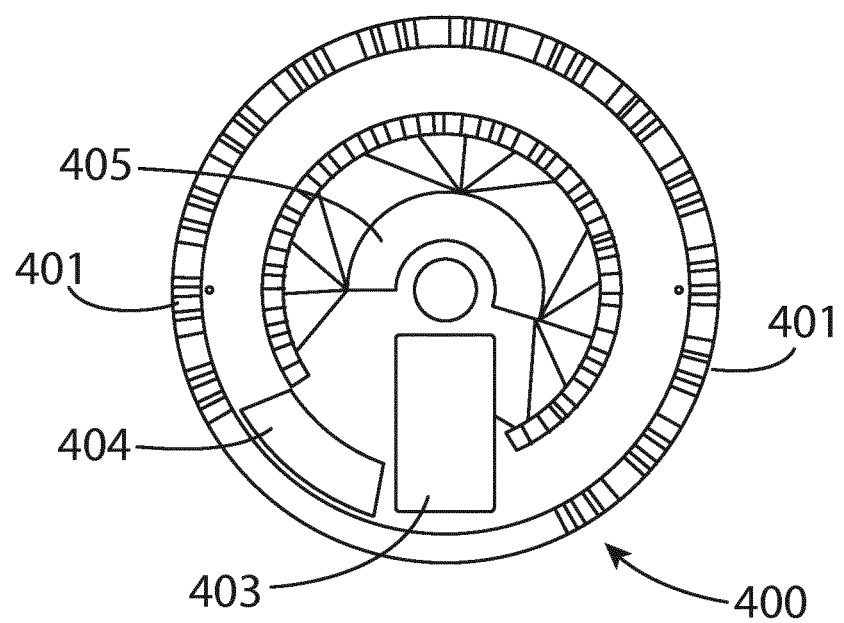
FIG. 10 show images of the MultiPlex device with inserted electrodes for bacterial capture and detection.

In this example, the Multiplex device 400 is comprised solely of one testing area. For example, following bacteria diagnosis from the Binary response device determination (Gram positive, Gram negative or yeast), the multiplex device provides the capability of determining the bacteria subspecies for either a Gram positive or Gram negative pathogen containing sample. With reference to FIG. 10, this device 400 comprises 14 distinct electrode incubation chambers 401. There is an arrangement comprising ITO-Au—Au electrode arrangement in each of the 14 incubation chambers 401. Each incubation chamber is functionalized with a specific capture antibody. Table 1 below shows a list of examples of gram positive detection possibilities in a single device.

TABLE 1

| Electrode Chamber | Gram + Bacteria |
| --- | --- |
| 1 | *Clostridium perfringens* |
| 2 | *Enterococcus casseliflavus* |
| 3 | *Enterococcus faecalis* |
| 4 | *Enterococcus faecium* |
| 5 | *Enterococcus gallinarum* |
| 6 | *Listeria monocytogenes* |
| 7 | *Propionibacterium acnes* |
| 8 | *Staphylococcus aureus* |
| 9 | *Staphylococcus epidermidis* |
| 10 | *Staphylococcus agalactiae* |
| 11 | *Staphylococcus dysgalactiae* |
| 12 | *Staphylococcus equisimilis* |
| 13 | *Staphylococcus pneumoniae* |
| 14 | *Staphylococcus pyogenes* |

The skilled person will appreciate that the device may be modified for the capture and detection of various types of gram positive, gram negative and fungal pathogens. Examples of such gram positive pathogens include *Staphylococcus aureus*, CoNS (Coagulase negative Staphylococci), *Streptococcus pneumoniae, Streptococcus* spp, *Enterococcus faecium* and *Enterococcus faecalis*. Examples of such gram negative pathogens include *Escherichia coli,* *Klebsiella (pneumoniae/oxytoca), Serratia marcescens, Enterobacter (cloacae/aerogenes), Proteus mirabilis, Pseudomonas aeruginosa, Acinetobacter baumannii* and *Stenotrophomonas maltophilia*. Examples of fungal pathogens include *Candida albicans, Candida tropicalis, Candida parapsilosis, Candida krusei, Candida glabrate* and *Aspergillus fumigatus*.

In this example, a 5 ml whole blood sample is loaded into the blood separation chamber 403. The blood is loaded and a spin rate applied. The blood separation can take from 6-9 minutes to separate. Once ready, the spin rate of the disc is increased to wet and break the blood separation chamber's DF tab. The spin rate is reduced to allow the plasma to fill up each of the chambers and allow for a slow steady flow through the fourteen electrode incubation chambers. A long microchannel connects the final electrode chamber to the waste chamber. The flow rate of the plasma into the waste chamber 404 is controlled using a known width of channel. Increasing the size of this channel increases the exit flow rate of the sample. The incubation time varies from 7-9 minutes. A dissolvable film (DF) tab is located in the waste chamber. Once burst, the lower-channel air pressure is released and the wash chamber's DF tab is now in a burstable state. The spin rate is increased to burst the wash buffer reservoir 405 located directly above the electrode chambers. A series of lower channels links the wash buffer reservoir 405 to the electrode chambers 401. The spin rate is reduced and the wash buffer flows through each of the electrode chambers 401 into the waste chamber 405. The device is removed from the spin stand mechanism where it is then attached to a potentiostat for detection.

8. Electrochemical Detection of Bacteria

The device and method according to the present teaching allows captured pathogens to be detected using electrochemical impedance thus eliminating the 7-48 hour culture step of conventional known assays.

Figure 13:
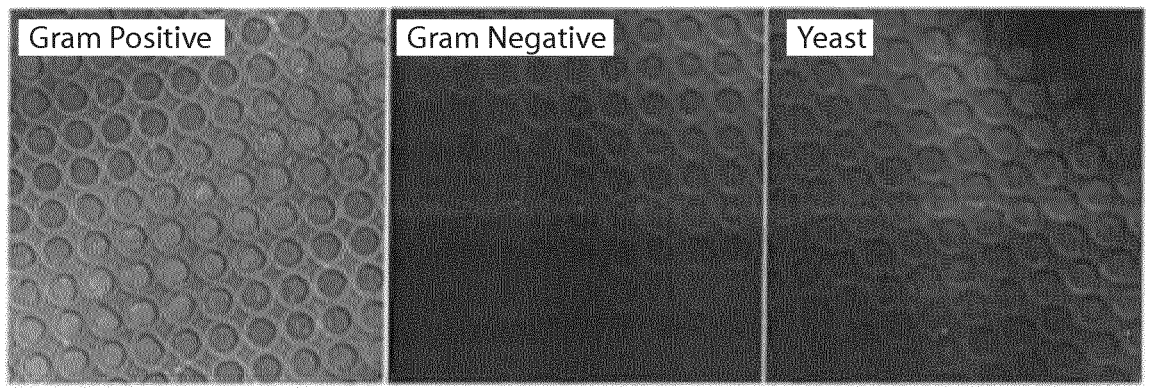
FIG. 13 shows confocal images of highly selective capture of pathogens from whole patient blood sample onto a photolithography cavity array substrate surface using a PDMS stamp using a 10-minute incubation time and 2 Minute Read Time within the microfluidic incubation chamber.

The present inventors have developed the technology to fabricate the microcavity array, selectively functionalise the top surface and cavity interiors and have demonstrated the capture of cells and developed an impedance based protocol for the detection of small numbers of cells (<10 cells) on electrodes. With reference to FIGS. 11A and 13, the array of microcavities 500 fabricated by electrodeposition or photolithography (for mass production) in accordance with the present teaching efficiently captures pathogens 501 from whole blood and detects them within 15 minutes using electrochemical impedance. In the example described herein and with reference to FIG. 11A, antibodies 502 to capture pathogens 501 are selectively immobilised on the surface of the array using a PDMS stamp. Cell capture "plugs" or blocks the opening 503 to the microcavity resulting in an unexpectedly larger change in impedance compared to conventional planar surfaces. At low electrolyte concentrations, the double layer thickness is increased so that the interfacial electric field interacts with the bound cells, rather than just with the antibody capture layer.

With reference to FIG. 11B, the analyte may comprise a single pathogen 504 or a colony 505 of pathogens whereby depending on the diameter of the cavity and the size of the analyte, the captured analyte "plugs" or blocks the opening to the cavity by either "plugging" inside the cavity 503 or by being immobilised across the opening of the cavity thereby blocking the opening to the cavity.

It has been determined that 2 micron cavities are the optimal size for pathogen capture as the pathogens may vary from 1-3 micron in size and can exist as single cells (1-3 micron in size) and colonies (2+ cells/aggregated cells 3-10 micron in size) in any given fluid. The single cells tend to "plug" inside the cavity while the larger colony/aggregates which are bigger than the 2 micron cavity diameter go across and "block" the cavity.

Figure 12:
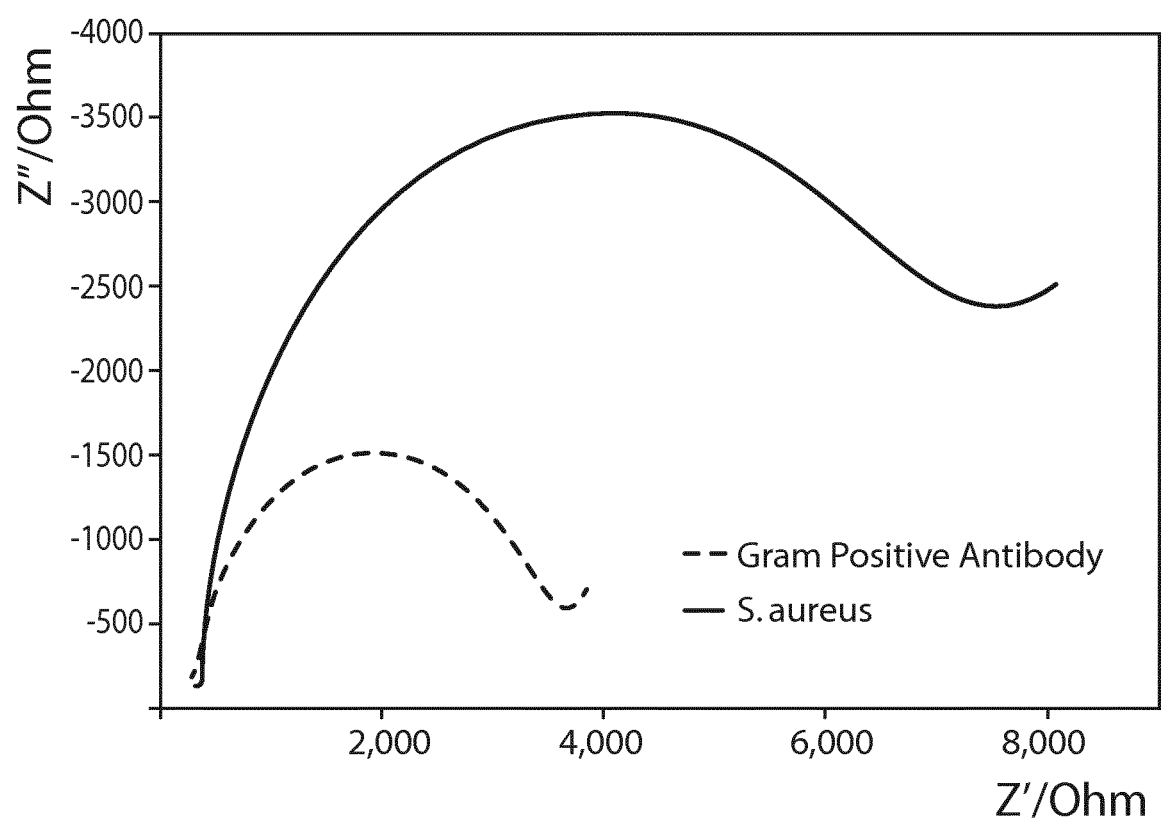
FIG. 12 is an impedance spectrum presenting a significant change in impedance following successful capture of *S. aureus* pathogens at the gram positive modified array surface.

The device according to the present teaching detects pathogens by measuring the non-faradaic impedance in the presence of a dilute phosphate buffered saline solution. Using a highly efficient antibody capture layer and impedance based detection in a dilute electrolyte solution maximises the double layer thickness and increases the impedance change observed when cells are captured driving down the limit of detection. In electrochemical impedance, the Nyquist plot consists of an imaginary (Z") and real (Z') impedance and can be fitted to decouple changes in the solution phase resistance as well as resistance associated with the antibody layer or the capture of pathogens, see FIG. 12. The impedance response is measured in a solution of DPBS with a frequency range from 0.01 Hz to 100 kHz inside a Faraday cage to detect bacteria. FIG. 14 shows a Nyquist plot (top) and a bode plot (bottom) which demonstrate significant changes in impedance following pathogen capture.

It will be appreciated that what we have described here are two examples of a microfluidic disc where a plurality of chambers may be selectively blocked so as to change a response characteristic of a device indicative of the presence or otherwise of a target analyte. In a first aspect, the response characteristic is a binary response characteristic providing the user with an initial overview of the presence or otherwise of particular target analytes. In a second aspect, the response characteristics can be more directly tuned to the presence of particular types of analytes. In this way, the device can give a more granular or detailed information on a subtype of analyte. Therefore, particular disks can be provided for a genus type determination and further disks can be provided for analysis of a genus subtype having determined the genus.

The microfluidic device according to the present teaching allows for ultrasensitive, direct (no amplification of target, e.g., by blood culture) detection of an analyte. This approach is attractive for near point-of-use applications by rapidly providing easily interpreted information that directly influences decision making.

The binary response device according to the present teaching has been used to detect the presence of gram positive, gram negative, fungal species and mixtures thereof in blood culture samples. Pathogens which have been correctly identified by the device as being gram positive, gram negative or fungal species include, for example, *Capnocytophaga gingivalis, Staphylococcus epidermis, E. coli, Staphylococcus hominis, Streptococcus mitis oralis, Enterococcus faecalium*, Clostridia, gram negative with *Enterococcus faecalis, Paenibacillus pabuli* and *Staphlococci haemolyticus*. The device described herein enables the detection of such pathogens within a period of 15 minutes.

The device provides for multiplexed detection of a number of different analytes within a single microfluidic, sample-to-answer device.

The device enables the rapid assessment of health or environmental threats through a short analysis time since the signal, not the target is amplified.

Furthermore, the microfluidic device described provides for the accurate assessment of disease stage and prognosis since a wide dynamic range will be achieved by tuning the size of the detecting surface (fewer cavities) so that the same fraction of its surface is covered by analyte (key determinant of S/N ratio) even for ultralow concentrations (<pM) of the analyte in solution.

The device is advantageous in that it is a robust and low cost device. It utilises low power, simple electronics and a rugged electrochemical or optical transduction methodology. These features enable low cost production, maintenance and repair of the reader using technology similar to that used in blood glucose monitors.

A further advantage of the device is that it provides a "Sample-to-answer device" in which reagents are held within the device and their release triggered at the appropriate time. Thus, no additional reagents need to be added other than the sample itself minimizing operator error/contamination which as discussed above is a particular challenge in detecting low analyte concentrations.

The words comprises/comprising when used in this specification are to specify the presence of stated features, integers, steps or components but does not preclude the presence or addition of one or more other features, integers, steps, components or groups thereof.

The invention claimed is:

1. A microfluidic device for detection of at least one biological cell within a fluid, the device comprising a sample chamber for receiving the fluid, a detection chamber, and a waste reservoir, each of the sample chamber, detection chamber and waste reservoir being in fluid communication with one another such that the received fluid can pass from the sample chamber through the detection chamber to the waste reservoir, the microfluidic device further comprising a substrate having a first surface defining entrances to a plurality of chambers defined in the substrate, the plurality of chambers forming a microcavity array within the detection chamber, surfaces of the chambers defining a second surface of the substrate, the first surface configured to selectively target and capture the at least one biological cell and thereby operably effect a blocking of the entrance to at least one of the chambers by either plugging an inside of the chamber or by immobilizing the at least one biological cell across an opening of the chamber, the device further comprising an electrode arrangement configured to provide an electrochemical output response characteristic and wherein the electrochemical output response characteristic of the microfluidic device as provided by the electrode arrangement is operably varied by the blocking of the entrance to the at least one of the chambers by the biological cell, thereby providing an indication of the presence of an analyte within the fluid.

2. A microfluidic device according to claim 1 wherein the first surface is selectively modified to inhibit non-specific capture of the at least one biological cell.

3. A microfluidic device according to claim 1 wherein the biological cell comprises a pathogen, cancer cell, or other rare cell.

4. A microfluidic device according to claim 1, wherein the first surface of said substrate is modified by immobilising a capture agent on said surface.

5. A microfluidic device according to claim 4, wherein the capture agent is selected from the group consisting of antibodies, protein, nucleic acid or synthetic receptor.

6. A microfluidic device according to claim 4 wherein said capture agent is immobilised on the first surface by means of wet chemical deposition, cold plasma deposition or soft stamping onto said surface.

7. A microfluidic device according to claim 4 wherein the capture agent is located on said first surface around an entrance of said one or more chambers.

8. A microfluidic device according to claim 1 wherein surfaces of the chambers defined in the substrate define a curved surface.

9. A microfluidic device according to claim 1 wherein the one or more chambers defined in the substrate have a diameter or width in the range 100 nm to 10 µm.

10. A microfluidic device according to claim 1 wherein the one or more chambers have a depth between 0.05 and 0.95 times a diameter of the chamber.

11. A microfluidic device according to claim 10 wherein individual chambers of the microcavity array have different sizes.

12. A microfluidic device according to claim 1 wherein a size and shape of said one or more chambers is selected to match that of said target biological cell.

13. A microfluidic device according to claim 1 wherein the chambers of the microcavity array are laterally spaced such that a spacing between the chambers is optimised for the selective capture of the biological cell to be detected.

14. A microfluidic device according to claim 13 wherein a separation or pitch between the chambers is between 0 and 100 times a diameter or width of the chamber.

15. A microfluidic device according to claim 3, wherein the biological cell comprises a pathogen selected from the group consisting of gram positive bacteria, gram negative bacteria and fungi.

16. A microfluidic device according to claim 1, wherein an internal surface of each chamber is modified for detection of a molecular marker such that an electrochemical output response characteristic of the microfluidic device is operably varied by the binding of a released marker into at least one of the chambers thereby providing an indication of the properties of the cell captured.

17. A microfluidic device according to claim 16, wherein the molecular marker comprises a small molecule, nucleic acid or a protein.

18. A microfluidic device according to claim 16 wherein the internal surface of each chamber is functionalised with a capture agent.

19. A microfluidic device according to claim 18 wherein the capture agent is selected from the group consisting of DNA or RNA capture strands, antibodies or a synthetic capture agent.

20. A microfluidic device according to claim 1 wherein the electrochemical output response characteristic of the microfluidic device is operably varied upon capture of an analyte followed by marker release thereby indicating the presence of an analyte within the fluid.

21. A microfluidic device according to claim 1 wherein the electrochemical output response comprises a changed electrochemical impedance signal which provides an indication of a pathogen load within the fluid.

22. A microfluidic device according to claim 1 wherein the fluid is selected from the group consisting of a liquid sample, a whole blood sample, urine, saliva, blood plasma or other fraction, interstitial fluid, cerebrospinal fluid, liquidised food sample or extracted from a surface swab.

23. A microfluidic device according to claim 1 wherein said analyte is captured and detected within a time period in the range 1 to 60 minutes.

24. A microfluidic device according to claim 23 wherein the time period for capture is greater than the time period for subsequent detection of a captured pathogen.

25. A microfluidic device according to claim 1 wherein the device can detect cells at concentrations of about 2 cells/ml.

26. A method of detecting an analyte in a fluid comprising the use of the microfluidic device according to claim 1.

27. A method of detecting an analyte in a fluid sample, the method comprising:
   (i) introducing a sample to the microfluidic device of claim 1,
   (ii) inducing a fluid flow,
   (iii) capturing an analyte; and
   (iv) detecting the presence of the analyte in the fluid by measuring a variation in a response characteristic of the microfluidic device.

28. A method according to claim 27 further comprising measuring the release of a marker from the captured entity.

29. A method according to claim 27 wherein the analyte comprises a pathogen, cell, vesicle or exosome.

30. A method according to claim 27, wherein the electrochemical output response characteristic of the microfluidic device is operably varied upon capture of an analyte in the fluid.

31. A method according to claim 30 wherein the electrochemical output response comprises an impedance signal which is operably varied upon capture of the analyte.

32. A microfluidic disc comprising a microfluidic device according to claim 1.

* * * * *